US010590097B2

(12) United States Patent
Mollenkopf et al.

(10) Patent No.: US 10,590,097 B2
(45) Date of Patent: *Mar. 17, 2020

(54) ACESULFAME POTASSIUM COMPOSITIONS AND PROCESSES FOR PRODUCING SAME

(71) Applicant: Celanese International Corporation, Irving, TX (US)

(72) Inventors: Christoph Mollenkopf, Frankfurt am Main (DE); Peter Groer, Babenhausen (DE); Arvind Yadav, Hessen (IN)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/273,404

(22) Filed: Feb. 12, 2019

(65) Prior Publication Data

US 2019/0169145 A1 Jun. 6, 2019

Related U.S. Application Data

(63) Continuation of application No. 16/014,510, filed on Jun. 21, 2018, now Pat. No. 10,227,316, which is a continuation of application No. 15/704,419, filed on Sep. 14, 2017, now Pat. No. 10,030,000.

(60) Provisional application No. 62/397,528, filed on Sep. 21, 2016, provisional application No. 62/397,520, filed on Sep. 21, 2016.

(51) Int. Cl.
C07D 209/06 (2006.01)
C07D 291/06 (2006.01)
A23L 27/30 (2016.01)

(52) U.S. Cl.
CPC ............ C07D 291/06 (2013.01); A23L 27/30 (2016.08); A23L 27/31 (2016.08); A23V 2002/00 (2013.01)

(58) Field of Classification Search
CPC .............................. C07D 209/06; A23L 27/30
USPC ......................................................... 544/200
See application file for complete search history.

(56) References Cited

U.S. PATENT DOCUMENTS

| | | |
|---|---|---|
| 4,563,521 A | 1/1986 | Clauss et al. |
| 4,607,100 A | 8/1986 | Clauss et al. |
| 4,638,063 A | 1/1987 | Clauss et al. |
| 4,695,629 A | 9/1987 | Clauss et al. |
| 4,804,755 A | 2/1989 | Reuschling et al. |
| 4,806,639 A | 2/1989 | Reuschling et al. |
| 4,876,341 A | 10/1989 | Schütz et al. |
| 5,011,982 A | 4/1991 | Clauss et al. |
| 5,084,180 A | 1/1992 | Boateng |
| 5,103,046 A | 4/1992 | Clauss et al. |
| 5,334,397 A | 8/1994 | Ream et al. |
| 5,744,010 A | 4/1998 | Roscher et al. |
| 5,808,159 A | 9/1998 | Giebeler |
| 7,408,059 B2 | 8/2008 | Kobayashi et al. |
| 7,977,514 B2 | 7/2011 | Peters et al. |
| 8,182,756 B2 | 5/2012 | Liu et al. |
| 8,303,921 B2 | 11/2012 | Brietzke et al. |
| 8,309,048 B2 | 11/2012 | Brietzke et al. |
| 8,496,905 B2 | 7/2013 | Brietzke et al. |
| 8,658,830 B2 | 2/2014 | Brietzke et al. |
| 9,024,016 B2 | 5/2015 | Bayer et al. |
| 10,023,456 B1 | 7/2018 | Mollenkopf et al. |
| 10,029,998 B2 | 7/2018 | Mollenkopf et al. |
| 10,029,999 B2 | 7/2018 | Mollenkopf et al. |
| 10,030,000 B2 * | 7/2018 | Mollenkopf ............ A23L 27/30 |
| 10,227,316 B2 * | 3/2019 | Mollenkopf ............ A23L 27/30 |
| 2003/0065172 A1 | 4/2003 | Tian et al. |
| 2003/0065218 A1 | 4/2003 | Mollenkopf |
| 2008/0076919 A1 | 3/2008 | Liu et al. |
| 2009/0318685 A1 | 12/2009 | Saito et al. |
| 2009/0318686 A1 | 12/2009 | Saito et al. |
| 2010/0274057 A1 | 10/2010 | Peters et al. |
| 2011/0256045 A1 | 10/2011 | Brietzke et al. |
| 2011/0256046 A1 | 10/2011 | Brietzke et al. |
| 2013/0062192 A1 | 3/2013 | Brietzke et al. |

(Continued)

FOREIGN PATENT DOCUMENTS

| | | |
|---|---|---|
| CA | 1273923 | 9/2009 |
| CN | 85104277 | 6/1985 |

(Continued)

OTHER PUBLICATIONS

Duan et al., "Synthesis of Acesulfame Potassium," *Fine Chemicals*, vol. 13, 1996, pp. 22-24.

ASTM E 313-05, Standard Practice for Calculating Yellowness and Whiteness Indices from Instrumentally Measured Color Coordinates, Oct. 1, 2005, 6 pages.

Boehshar et al., 5- Chloroacesulfame K- a characteristic indicator for application of the "sulfur trioxide" process in the manufacture of acesulfame K, Research Disclosure, 2003, 477036.

Mayer et al., Acesulfame-K, Food Science and Technology, Jun. 28, 1991.

(Continued)

*Primary Examiner* — Kahsay Habte
(74) *Attorney, Agent, or Firm* — Dority & Manning, P.A.

(57) ABSTRACT

A process for producing acesulfame potassium, the process comprising the steps of providing a cyclizing agent composition comprising a cyclizing agent and a solvent and having an initial temperature, cooling the cyclizing agent composition to form a cooled cyclizing agent composition having a cooled temperature less than 35° C., reacting an acetoacetamide salt with the cyclizing agent in the cooled cyclizing agent composition to form a cyclic sulfur trioxide adduct composition comprising cyclic sulfur trioxide adduct; and, forming from the cyclic sulfur trioxide adduct in the cyclic sulfur trioxide adduct composition the finished acesulfame potassium composition comprising non-chlorinated acesulfame potassium and less than 39 wppm 5-chloro-acesulfame potassium. The cooled temperature is at least 2° C. less than the initial temperature.

17 Claims, 1 Drawing Sheet

(56) References Cited

U.S. PATENT DOCUMENTS

| | | |
|---|---|---|
| 2013/0331565 A1 | 12/2013 | Bayer et al. |
| 2018/0297967 A1 | 10/2018 | Mollenkopf et al. |
| 2018/0297968 A1 | 10/2018 | Mollenkopf et al. |
| 2018/0297970 A1 | 10/2018 | Mollenkopf et al. |

FOREIGN PATENT DOCUMENTS

| | | |
|---|---|---|
| CN | 85104277 A | 12/1986 |
| CN | 1883790 | 12/2006 |
| CN | 200949088 | 9/2007 |
| CN | 101124981 | 2/2008 |
| CN | 101124981 A | 2/2008 |
| CN | 101148300 | 3/2008 |
| CN | 101157666 | 4/2008 |
| CN | 101787001 | 7/2010 |
| CN | 101913898 | 12/2010 |
| CN | 201921689 | 8/2011 |
| CN | 102225333 | 10/2011 |
| CN | 102359926 | 2/2012 |
| CN | 102380226 | 3/2012 |
| CN | 102380266 A | 3/2012 |
| CN | 202221403 U | 5/2012 |
| CN | 102866042 | 1/2013 |
| CN | 103018368 | 4/2013 |
| CN | 103130743 | 6/2013 |
| CN | 10331294 | 10/2013 |
| CN | 103570592 | 2/2014 |
| CN | 103570592 A | 2/2014 |
| CN | 103588728 | 2/2014 |
| CN | 103588728 A | 2/2014 |
| CN | 103613566 | 3/2014 |
| CN | 103613566 A | 3/2014 |
| CN | 103960558 | 8/2014 |
| CN | 104193625 | 12/2014 |
| CN | 104209052 | 12/2014 |
| CN | 104225956 | 12/2014 |
| CN | 104292181 | 1/2015 |
| CN | 104292181 A | 1/2015 |
| CN | 204320227 | 5/2015 |
| CN | 105085160 A | 11/2015 |
| CN | 105111166 A | 12/2015 |
| CN | 105152446 | 12/2015 |
| CN | 105198778 | 12/2015 |
| CN | 106262665 | 1/2017 |
| CN | 106267879 | 1/2017 |
| CN | 106346138 | 1/2017 |
| CN | 106349009 | 1/2017 |
| CN | 106349190 | 1/2017 |
| CN | 106349191 | 1/2017 |
| CN | 106349300 | 1/2017 |
| CN | 106365952 | 2/2017 |
| CN | 106496159 A | 3/2017 |
| CN | 206001191 | 3/2017 |
| CN | 206001201 | 3/2017 |
| CN | 206001439 | 3/2017 |
| CN | 206121215 | 4/2017 |
| DE | 1249262 | 10/1966 |
| DE | 1268141 | 5/1968 |
| DE | 3522470 | 1/1987 |
| DE | 3531357 | 3/1987 |
| DE | 3545196 | 6/1987 |
| EP | 0155634 | 9/1985 |
| EP | 0159516 | 10/1985 |
| EP | 0215347 | 3/1987 |
| EP | 0217024 | 4/1987 |
| EP | 0218076 | 4/1987 |
| JP | 54032406 | 3/1979 |
| JP | S 5432406 A | 3/1979 |
| WO | WO93/19055 | 9/1993 |
| WO | WO 2011/133468 A1 | 10/2011 |
| WO | WO2013/182651 | 12/2013 |

OTHER PUBLICATIONS

International Search Report received in the corresponding International PCT Patent application No. PCT/US2007/051507, dated Nov. 9, 2017.

Linkies et al., Synthesis, 1990, 5, 405-406.

"Commission Direction 95/31/EC of Jul. 5, 1995 laying down specific criteria of purity concerning sweeteners for use in foodstuff," Official Journal of the European Communities, Jul. 28, 1995, 19 pages.

"Commission Direction 2008/60/EC of Jun. 17, 2008 laying down specific purity criteria concerning sweeteners for use in foodstuffs," Official Journal of the European Union, Jun. 18, 2008, 40 pages.

"Regulations—Commission Regulation (EU) No. 231/2012 of Mar. 9, 2012 laying down specifications for food additives listed in Annexes II and II to Regulation (EC) No. 1333/2008 of the European Parliament and of the Council," Official Journal of the European Union, Mar. 22, 2012, 295 pages.

Opinion—"Re-evaluation of acesulfame K with reference to the previous SCF opinion of 1991," European Commission , Health & Consumer Protection Directorate—General, Directorate B—Scientific Health Opinions, Unit B3—Management of Scientific Committees II, Scientific Committee on Food, Mar. 13, 2000, 8 pages.

Product Information on "Acesulfame Potassium," 2001, 57th JECFA (joint FAO/WHO Expert Committee on Food Additives), FNP 52 Add 9, 2 pages.

Suenaga, "Ethylene-amine salt recovery—by converting the hydrochloride into the sulphate, and reacting with ammonia in aq. Solvent to ppte. Ammonium sulphate", WPI/Thompson, 1979, No. 16, XP 002598345 (See JP54032406).

Sunnett Brochure, "Acesulfame Potassium", Celanese, Apr. 2014.

Xiangsheng et al., "Synthesis of Acesulfame Potassium", Fine Chemicals, vol. 13, 1996, 1-15.

Information Disclosure Statement submitted Oct. 27, 2017, 2 pages.

Boehshar, Manfred & Burgard, Andreas. (2003). 5- Chloroacesulfame K—a characteristic indicator for application of the "sulfur trioxide" process in the manufacture of acesulfame K. Research Disclosure. 477036.

D. Mayer, et al., Acesulfame-K (Food Science and Technology), 1991, Intro., Chapters 15, 16, and 18, 56 pages.

\* cited by examiner

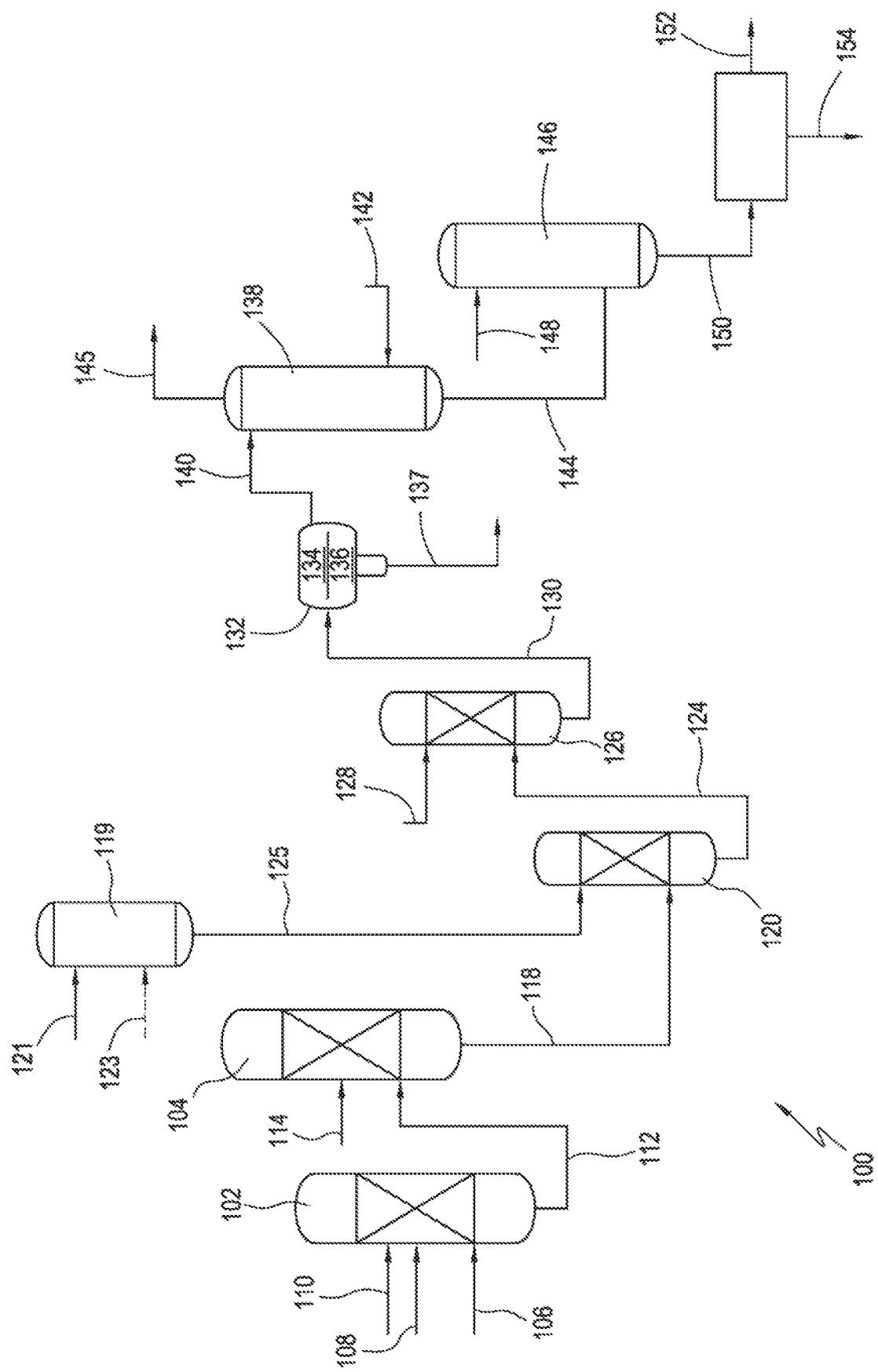

ACESULFAME POTASSIUM COMPOSITIONS AND PROCESSES FOR PRODUCING SAME

CROSS-REFERENCE TO RELATED APPLICATIONS

This application is continuation of U.S. application Ser. No. 16/014,510 having a filing date of Jun. 21, 2018, which is a continuation of U.S. application Ser. No. 15/704,419 having a filing date of Sep. 14, 2017 now U.S. Pat. No. 10,030,000), which claims priority to U.S. Provisional Patent Application No. 62/397,528, filed Sep. 21, 2016, and to U.S. Provisional Patent No. 62/397,520, filed Sep. 21, 2016, the entireties of which are incorporated herein by reference.

FIELD OF INVENTION

The present invention relates generally to acesulfame potassium and to processes for producing acesulfame potassium. More specifically, the present invention relates to processes for producing high purity acesulfame potassium.

BACKGROUND OF THE INVENTION

Acesulfame potassium has an intense, sweet taste and has been used in many food-related applications as a sweetener. In conventional acesulfame potassium production processes, sulfamic acid and an amine, e.g., triethylamine, are reacted to form an amidosulfamic acid salt, such as a trialkyl ammonium amidosulfamic acid salt. The amidosulfamic acid salt is then reacted with diketene to form an acetoacetamide salt. The acetoacetamide salt may be cyclized, hydrolyzed, and neutralized to form acesulfame potassium. U.S. Pat. Nos. 5,744,010 and 9,024,016 disclose exemplary acesulfame potassium production processes.

Typically, the acetoacetamide salt intermediate is cyclized by reaction with sulfur trioxide in an inorganic or organic solvent to form a cyclic sulfur trioxide adduct. The solvent routinely utilized in this reaction is an organic solvent such as a halogenated, aliphatic hydrocarbon solvent, for example, dichloromethane. The adduct formed by this reaction is subsequently hydrolyzed and then neutralized with potassium hydroxide to form acesulfame potassium.

Acesulfame potassium and the intermediate compositions produced by conventional methods contain undesirable impurities, such as 5-chloro-acesulfame potassium. Limits for the content of various impurities are often set by governmental regulations or customer guidelines. Due to their similar chemical structures and properties, separation of 5-chloro-acesulfame potassium from the desired non-chlorinated acesulfame potassium, using standard purification procedures such as crystallization has proven difficult, resulting in consumer dissatisfaction and the failure to meet regulatory standards.

The need exists for an improved process for producing high purity acesulfame potassium compositions in which the formation of 5-chloro-acesulfame potassium during synthesis is reduced or eliminated.

All of the references discussed herein are hereby incorporated by reference.

SUMMARY OF THE INVENTION

The application discloses processes for producing a finished acesulfame potassium composition, the process comprising the steps of providing a cyclizing agent composition comprising a cyclizing agent and a solvent and having an initial temperature, cooling the cyclizing agent composition to form a cooled cyclizing agent composition having a cooled temperature less than 35° C., reacting an acetoacetamide salt with the cyclizing agent in the cooled cyclizing agent composition to form a cyclic sulfur trioxide adduct composition comprising cyclic sulfur trioxide adduct; and forming from the cyclic sulfur trioxide adduct in the cyclic sulfur trioxide adduct composition the finished acesulfame potassium composition comprising non-chlorinated acesulfame potassium and less than 39 wppm 5-chloro-acesulfame potassium, e.g., from 1 wppb to 5 wppm 5-chloro-acesulfame potassium. The cooled temperature is at least 2° C. less than the initial temperature. The finished acesulfame potassium composition may comprise at least 90% by weight of the 5-chloro-acesulfame potassium present in the crude acesulfame potassium composition. The forming of the finished acesulfame potassium composition from the cyclic sulfur trioxide adduct may comprise the steps of hydrolyzing the cyclic sulfur trioxide adduct in the cyclic sulfur trioxide adduct composition to form an acesulfame-H composition and neutralizing the acesulfame-H in the acesulfame H composition to form a crude acesulfame potassium composition comprising non-chlorinated acesulfame potassium and less than 39 wppm 5-chloro-acesulfame potassium, and forming the finished acesulfame potassium composition from the crude acesulfame potassium composition. The forming of the finished acesulfame potassium composition may comprise the steps of concentrating the crude acesulfame composition to form an intermediate acesulfame potassium composition comprising at least 10 wt % acesulfame potassium and separating the intermediate acesulfame potassium composition to form the finished acesulfame potassium composition comprising at least 15 wt % acesulfame potassium. The provision of the cyclizing agent composition may comprise the step of contacting the solvent and the cyclizing agent to form the cyclizing agent composition, and a contact time from the beginning of the contacting step to the beginning of reacting step (c) may be less than 60 minutes. In some case, the cooled cyclizing agent composition has a cooled temperature less than 25° C., the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. In some cases, the cooled cyclizing agent composition has a cooled temperature ranging from −35° C. to 15° C., the crude acesulfame potassium composition comprises from 1 wppb to 5 wppm 5-chloro-acesulfame potassium, and the finished acesulfame potassium composition comprises from 1 wppb to 2.7 wppm 5-chloro-acesulfame potassium. In some cases, the cooled cyclizing agent composition has a cooled temperature less than 25° C., the contact time is less than 15 minutes, the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. In some cases, the cooled cyclizing agent composition has a cooled temperature ranging from −35° C. to 15° C., the contact time is less than 5 minutes, the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. In some embodiments, the cooled cyclizing agent composition comprises less than 1 wt % cyclizing agent/solvent reaction product selected from the group consisting of chloromethyl chlorosulfate and methylbis-chlorosulfate and/or the weight ratio of solvent to cyclizing agent in the cyclizing agent composition is at least 1:1. In one embodiment, the process comprises the steps of providing a solvent, cooling the solvent, combining the cooled solvent with a cyclizing agent to form a cooled cyclizing agent composition having a cooled temperature less than 35° C., reacting an acetoacetamide salt with the cyclizing agent in the cyclizing agent composition to form a cyclic sulfur trioxide adduct composition, and forming from the cyclic sulfur trioxide adduct composition the finished acesulfame potassium composition. In another aspect, the disclosure relates to a process for producing a finished acesulfame potassium composition, the process comprising the steps of providing a cyclic sulfur trioxide adduct composition comprising one or more of chloromethyl chlorosulfate and methyl-bis-chlorosulfate present in a collective amount less than 1 wt %; and forming the finished acesulfame potassium composition from the cyclic sulfur trioxide adduct composition. The provision of the cyclic sulfur trioxide adduct composition may comprise the steps of reacting sulfamic acid and triethylamine to form an amidosulfamic acid salt, reacting the amidosulfamic acid salt and diketene to form acetoacetamide salt, providing a cyclizing agent composition comprising a sulfur trioxide and dichloromethane and having an initial temperature, cooling the cyclizing agent composition to form a cooled cyclizing agent composition having a cooled temperature below 35° C., and reacting the acetoacetamide salt with sulfur trioxide in the cooled cyclizing agent composition to form the cyclic sulfur trioxide adduct composition. Preferably, the cooled temperature is at least 2° C. less than the initial temperature. In some cases, the providing step comprises the step of contacting the solvent and the cyclizing agent to form the cyclizing agent composition and a contact time from the beginning of the contacting step to the beginning of the reacting step is less than 15 minutes, and the cooled cyclizing agent composition has a cooled temperature less than 25° C., the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. In some cases, the providing step comprises the step of contacting the solvent and the cyclizing agent to form the cyclizing agent composition and a contact time from the beginning of the contacting step to the beginning of the reacting step is less than 5 minutes, and the cooled cyclizing agent composition has a cooled temperature ranging from −35° C. to 15° C., the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. In one embodiment, the process comprises the steps of reacting sulfamic acid and triethylamine to form an amidosulfamic acid salt, reacting the amidosulfamic acid salt and diketene to form acetoacetamide salt, providing a cyclizing agent composition comprising a sulfur trioxide and dichloromethane and having an initial temperature, cooling the cyclizing agent composition to form a cooled cyclizing agent composition having a cooled temperature less than 35° C., reacting the acetoacetamide salt with sulfur trioxide in the cooled cyclizing agent composition to form a cyclic sulfur trioxide adduct, hydrolyzing the cyclic sulfur trioxide adduct to form an acesulfame-H composition comprising acesulfame-H, neutralizing the acesulfame-H in the acesulfame-H to form a crude acesulfame potassium composition comprising non-chlorinated acesulfame potassium and from 1 wppb to 39 wppm 5-chloro-acesulfame potassium acid, and treating the crude acesulfame potassium composition to form the finished acesulfame potassium composition comprising acesulfame potassium and less than 37 wppm acetoacetamide-N-sulfonic acid (the reacting, providing, and cooling steps can be performed in any order before the reaction of the acetoacetamide salt with sulfur trioxide). The cooled temperature may be at least 2° C. less than the initial temperature, and the providing step comprises the step of contacting the solvent and the cyclizing agent to form the cyclizing agent composition. Contact time may be less than 60 minutes. In some cases, contact time is less than 15 minutes, the cooled cyclizing agent composition has a cooled temperature less than 25° C., the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. In some cases, contact time is less than 5 minutes, the cooled cyclizing agent composition has a cooled temperature ranging from −35° C. to 15° C., the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium. The application also describes crude, intermediate, and finished acesulfame potassium composition produced by the processes described herein.

BRIEF DESCRIPTION OF THE DRAWINGS

The invention is described in detail below with reference to the appended drawing.

FIG. 1 is a process flow sheet of an acesulfame potassium production process in accordance with one embodiment of the present invention.

DETAILED DESCRIPTION OF THE INVENTION

Introduction

Conventional processes for producing acesulfame potassium involve reacting sulfamic acid and an amine in the presence of acetic acid to form an amidosulfamic acid salt. The amidosulfamic acid salt is then reacted with an acetoacetylating agent, e.g., diketene, to form an acetoacetamide salt. The acetoacetamide salt is reacted with a cyclizing agent, e.g., sulfur trioxide, to form a cyclic sulfur trioxide adduct. The cyclic sulfur trioxide adduct is then hydrolyzed and neutralized via conventional means to form a crude acesulfame potassium composition comprising acesulfame potassium. This composition is phase separated into aqueous and organic phases. Most of the acesulfame potassium separates into the aqueous phase. As used herein, the term "crude acesulfame potassium composition" refers to the initial product of a the neutralization reaction or to the aqueous phase that is formed from the phase separation step (without any further purification). The crude acesulfame potassium composition comprises at least 5 wt % acesulfame potassium. The crude acesulfame potassium composition may be optionally treated to form an "intermediate acesulfame potassium composition" and/or a "finished acesulfame potassium composition," which are discussed below.

Conventional acesulfame potassium compositions have been shown to comprise several undesirable impurities, among them 5-chloro-acesulfame potassium and acetoacetamide. Content limits for these compounds in the finished acesulfame potassium composition are often determined by industry purity standards and/or by standards established for the particular end use products that utilize acesulfame potassium as a sweetener. In some cases, limits for these impurities are determined by governmental regulations. For most applications, high acesulfame potassium purity levels are preferred. Because the chemical structure of 5-chloro-acesulfame potassium is similar to that of non-chlorinated acesulfame potassium, separation of 5-chloro-acesulfame potassium using standard purification procedures such as crystallization has proven difficult.

Without being bound by theory, it has now been discovered that the reaction of the cyclizing agent with the acetoacetamide salt to form the cyclic sulfur trioxide adduct may also involve side reactions that form the 5-chloro-acesulfame potassium impurity.

The use of specific reaction parameters, however, may advantageously reduce or eliminate 5-chloro-acesulfame potassium formation or the formation of its precursor, 5-chloro-acesulfame-H. In particular, it has now been discovered that utilizing a low temperature cyclizing agent composition and/or cooling the cyclizing agent composition, e.g., to a temperature less than 35° C., surprisingly reduces or eliminates 5-chloro-acesulfame potassium formation in the crude, intermediate, and finished acesulfame potassium compositions. In addition, the reduced impurity levels in these acesulfame potassium compositions reduce or eliminate the need for additional purification steps, resulting in overall improved process efficiency.

It is postulated that the reaction of the cyclizing agent, the solvent, and optionally other components may lead to the formation of chlorine/chloride-containing compounds. Exemplary cyclizing agent/solvent reaction products include halogen-containing compounds such as chlorine/chloride-containing compounds, e.g., chlorosulfates. These compounds, in turn, may react to chlorinate the acesulfame precursor acid, acesulfame-H, sometimes referred to as sweetener acid, or its precursors, e.g., acetoacetamide-N-sulfonate. By cooling the cyclizing agent composition (before the cyclization reaction) and optionally by limiting contact time, lower amounts of chlorine/chloride-containing compounds (e.g., chlorosulfates) are formed (as compared to the amount formed when higher temperatures, and optionally greater contact times, are employed). That is, lower temperatures and optionally shorter contact times have now been shown to retard the formation of chlorine/chloride-containing compounds, e.g., chlorosulfates. As a result of the lower temperatures, and optionally shorter contact times, in one embodiment, the cyclizing agent composition may have a low chlorine/chloride-containing compound content, e.g., a low chlorosulfate content, as discussed herein. The reduction or elimination of chlorine/chloride-containing compounds directly leads to the formation of high purity acesulfame compositions. Without being bound by theory, it is postulated that without limiting temperature (and optionally contact time) as described herein, resultant crude, intermediate, and finished acesulfame potassium compositions will detrimentally have greater amounts of 5-chloro-acesulfame potassium.

Additional specific terms that are used herein are now defined. "Contact time," as used herein, refers to the time period that the solvent contacts the cyclizing agent before formation of the cyclic sulfur trioxide adduct. Thus, contact time begins when at least some of the solvent contacts at least some the cyclizing agent to form the cyclizing agent/solvent mixture ("cyclizing agent composition"), and contact time ends when the acetoacetamide salt first contacts the cyclizing agent in the cyclizing agent composition.

"Cyclization reaction time," as used herein, refers to the time from the start of the acetoacetamide salt feed to the termination of the acetoacetamide salt feed. In some cases, if indicated, the cyclization reaction time may include additional time past the termination of the acetoacetamide salt feed, e.g., an extra 5 minutes or an extra minute.

"5-chloro-acesulfame potassium," as used herein, refers to the following molecule:

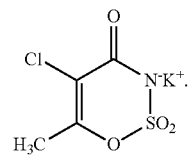

"Acetoacetamide," as used herein, refers to the following molecule:

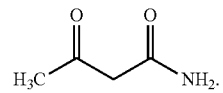

"Acetoacetamide-N-sulfonic acid" as used herein, refers to the molecule shown below. In some cases, acetoacetamide-N-sulfonic acid may be a degradation product of acesulfame potassium or acesulfame-H. The term "acetoacetamide-N-sulfonic acid," as used herein, also includes salts of acetoacetamide-N-sulfamic acid, e.g., potassium, sodium, and other alkali metal salts.

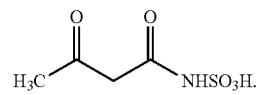

An "intermediate acesulfame potassium composition" refers to a composition resulting from the concentrating of the crude acesulfame potassium composition, e.g., the removal of water from the crude acesulfame potassium composition. The intermediate acesulfame potassium composition comprises at least 10 wt % acesulfame potassium, based on the total weight of the intermediate acesulfame potassium composition, and has an acesulfame potassium weight percentage that is higher than that of the crude acesulfame potassium composition.

A "finished acesulfame potassium composition" refers to a composition (preferably directly) resulting from the separating, e.g., crystallizing and/or filtering, of the intermediate acesulfame potassium composition. The finished acesulfame potassium composition comprises at least 15 wt % acesulfame potassium, based on the total weight percentage of the finished acesulfame potassium composition, and has an acesulfame potassium weight percentage that is higher than that of the intermediate acesulfame potassium composition.

"Wppm" and "wppb," as used herein, mean weight parts per million or weight parts per billion, respectively. These are based on the total weight of the respective composition, e.g., the total weight of the entire crude acesulfame potassium composition or the entire finished acesulfame potassium composition.

Acesulfame Potassium Formation (Cooled Cyclizing Agent Composition)

Processes for producing acesulfame potassium exhibiting high levels of purity is described herein.

In one embodiment, the process comprises the step of providing a cyclizing agent composition comprising a cyclizing agent and optionally a solvent (the formation of the cyclizing agent composition is discussed in more detail below). The cyclizing agent composition has an initial temperature, which typically will be an elevated temperature, e.g., greater than 35° C. The process further comprises the step of cooling the cyclizing agent composition to form a cooled cyclizing agent composition that has a cooled temperature. The cooled temperature is preferably at least 2° C. less than the initial temperature. In some embodiments the cooled temperature is less than 35° C.

Importantly, the cooled cyclizing agent composition is provided at a low temperature, e.g., lower than the initial temperature of the cyclizing agent composition. In one embodiment, the process further comprises the steps of reacting an acetoacetamide salt with the cyclizing agent in the cooled cyclizing agent composition to form a cyclic sulfur trioxide adduct composition. The process also comprises forming a finished acesulfame potassium composition from the cyclic sulfur trioxide adduct composition. As noted above, the cyclic sulfur trioxide adduct composition may be hydrolyzed and neutralized to yield a crude acesulfame potassium composition. Also, the crude acesulfame potassium composition may be treated, e.g., concentrated and separated to form the finished acesulfame potassium composition.

The reaction of the acetoacetamide salt and the cyclizing agent is conducted by contacting the two reactants, which are preferably fed, either separately or simultaneously (co-fed), to a reaction vessel. For example, the acetoacetamide salt may be added to the cyclizing agent composition, e.g., added drop-wise to the cyclizing agent composition. Alternatively, the cyclizing agent composition may be added to the acetoacetamide salt, e.g., added drop-wise to the acetoacetamide salt.

In some embodiments, the cooled cyclizing agent composition has a temperature less than 35° C., e.g., less than 32° C., less than 30° C., less than 25° C., less than 20° C., less than 15° C., less than 12° C., less than 11° C., less than 10° C., less than 8° C., less than 5° C., less than 3° C., less than 1° C., or less than 0° C. In terms of ranges, the cooled cyclization agent composition has a temperature ranging from −45° C. to 35° C., e.g., −45° C. to 25° C., −40° C. to 15° C., −35° C. to 15° C., −35° C. to 10° C., −30° C. to 25° C., −30° C. to 10° C., −15° C. to 25° C., from −15° C. to 15° C., from −10° C. to 12° C., from −8° C. to 10° C., or −8° C. to 5° C.

The initial temperature of the cyclizing agent composition may vary widely, as long as it is greater than the cooled temperature of the cooled cyclizing agent composition. In some embodiments, the cooling step reduces the temperature of the cyclizing agent composition (as initially provided), e.g., by at least 2° C., at least 3° C., at least 5° C., at least 10° C., at least 15° C., at least 20° C., or at least 25° C. In terms of ranges, the cooling step reduces the temperature of the cyclizing agent composition by from 2° C. to 70° C., e.g., from 3° C. to 65° C., from 5° C. to 50° C., from 5° C. to 35° C., or from 10° C. to 30° C.

In some embodiments, initial temperature of the cyclizing agent composition is less than 50° C., e.g., less than 40° C., less than 35° C., less than 25° C., less than 20° C., less than 15° C., less than 12° C., less than 11° C., or less than 10° C.

In terms of ranges, the initial temperature of the cyclizing agent composition ranges from −45° C. to 50° C., e.g., −45° C. to 40° C., −40° C. to 35° C., −35° C. to 15° C., −35° C. to 10° C., −30° C. to 25° C., −30° C. to 10° C., −15° C. to 25° C., from −15° C. to 15° C., from −10° C. to 12° C., from −8° C. to 10° C., or −8° C. to 5° C. In terms of lower limits, the initial temperature of the cyclizing agent composition may be at least −45° C., e.g., at least −35° C., at least −25° C., at least −15° C., at least 0° C., or at least 5° C.

In one embodiment, the process employs the aforementioned providing (or contacting), reacting, and forming steps. As a result of using these specific steps and parameters, the crude acesulfame potassium composition comprises from 0.001 wppm to 39 wppm 5-chloro-acesulfame potassium and the finished acesulfame potassium composition comprises from 0.001 wppm to 5 wppm 5-chloro-acesulfame potassium.

The cooling of the low temperature cyclizing agent composition or the provision of the low temperature cyclizing agent composition may be achieved through any of a variety of different cooling techniques. For example, the cooling step may be achieved by using one or more heat exchangers, refrigeration units, air cooling units, water cooling units, or a cooling medium, such as liquid nitrogen or other cryogenics. If heat exchangers are employed, a water/glycol mixture is a preferred exchange medium, with brine being a suitable alternative.

Cyclizing agent/solvent reaction products, e.g., chlorosulfates, undesireably may be formed when a cyclizing agent reacts with a chlorine-containing solvent in the cyclyizing agent composition. Exemplary chlorosulfates include chloromethyl chlorosulfate and methyl-bis-chlorosulfate.

It has now been discovered that by controlling the temperature of the cyclizing agent composition as discussed herein, fewer cyclizing agent/solvent reaction products, e.g., chlorosulfates, are formed. The cooled cyclizing agent composition, for example, may have a low cyclizing agent/solvent reaction product content, e.g., a low chlorosulfate content. For example, the cyclizing agent composition may comprise less than 1 wt % cyclizing agent/solvent reaction product, e.g., less than 0.75 wt %, less than 0.5 wt %, less than 0.25 wt %, less than 0.1 wt %, less than 0.05 wt %, or less than 0.01 wt %. In terms of ranges, the cyclizing agent composition may comprise from 1 wppm to 1 wt % cyclizing agent/solvent reaction products, e.g., from 10 wppm to 1 wt %, from 10 wppm to 0.75 wt %, from 10 wppm to 0.5 wt %, from 10 wppm to 0.25 wt %, from 100 wppm to 0.75 wt %, from 100 wppm to 0.5 wt %, or from 100 wppm to 0.25 wt %. These ranges and limits apply to cyclizing agent/solvent reaction products generally and to specific reaction products generally, e.g., chloromethyl chlorosulfate, methyl-bis-chlorosulfate, and combinations thereof.

In one embodiment, the cooled cyclizing agent composition comprises one or more of chloromethyl chlorosulfate and methyl-bis-chlorosulfate in a collective amount less than 1 wt %, e.g., less than 0.75 wt %, less than 0.5 wt %, less than 0.25 wt %, less than 0.1 wt %, less than 0.05 wt %, or less than 0.01 wt %. In one embodiment, the cyclizing agent composition comprises less than 1 wt % chloromethyl chlorosulfate, e.g., less than 0.75 wt %, less than 0.5 wt %, less than 0.25 wt %, less than 0.1 wt %, less than 0.05 wt %, or less than 0.01 wt %. In another embodiment, the cyclizing agent composition comprises less than 1 wt % methyl-bis-chlorosulfate, e.g., less than 0.75 wt %, less than 0.5 wt %, less than 0.25 wt %, less than 0.1 wt %, less than 0.05 wt %, or less than 0.01 wt %. In another embodiment, the cyclizing agent composition comprises both chloromethyl chlorosulfate and methyl-bis-chlorosulfate, collectively, in an amount less than 1 wt %, e.g., less than 0.75 wt %, less than 0.5 wt %, less than 0.25 wt %, less than 0.1 wt %, less than 0.05 wt %, or less than 0.01 wt %.

In some cases, the process comprises the steps of forming or providing a cyclic sulfur trioxide adduct composition comprising less than 1 wt % cyclizing agent/solvent reaction product, e.g., chloromethyl chlorosulfate and/or methyl-bis-chlorosulfate, and forming the finished acesulfame potassium composition from the cyclic sulfur trioxide adduct composition. The forming or providing of the cyclic sulfur trioxide adduct composition may vary widely as long as the cyclic sulfur trioxide adduct composition has the required cyclizing agent/solvent reaction product, e.g., chlorosulfate, content. Some methods of achieving the cyclic sulfur trioxide adduct composition include utilizing a cooled cyclizing agent composition in the reaction of the acetoacetamide salt with the cyclizing agent, as discussed herein. This method of achieving the cyclic sulfur trioxide adduct composition is merely exemplary and is not meant to limit the scope of the process, and other suitable methods are contemplated.

Thus, the use of a cooled cyclizing agent composition may result in the formation of a cyclic sulfur trioxide adduct composition having a low cyclizing agent/solvent reaction product content, e.g., a low chlorosulfate content. For example, the cyclic sulfur trioxide adduct composition may comprise less than 1 wt % cyclizing agent/solvent reaction product, e.g., less than 0.75 wt %, less than 0.5 wt %, less than 0.25 wt %, less than 0.1 wt %, less than 0.05 wt %, or less than 0.01 wt %. In terms of ranges, the cyclic sulfur trioxide adduct composition may comprise from 1 wppm to 1 wt % cyclizing agent/solvent reaction products, e.g., from 10 wppm to 1 wt %, from 10 wppm to 0.75 wt %, from 10 wppm to 0.5 wt %, from 10 wppm to 0.25 wt %, from 100 wppm to 0.75 wt %, from 100 wppm to 0.5 wt %, or from 100 wppm to 0.25 wt %.

In one embodiment, the cyclic sulfur trioxide adduct composition comprises one or more of chloromethyl chlorosulfate and methyl-bis-chlorosulfate in a collective amount less than 1 wt %, e.g., less than 0.75 wt %, less than 0.5 wt %, less than 0.25 wt %, less than 0.1 wt %, less than 0.05 wt %, or less than 0.01 wt %. In one embodiment, the cyclic sulfur trioxide adduct composition comprises less than 1 wt % chloromethyl chlorosulfate, e.g., less than 0.75 wt %, less than 0.5 wt %, less than 0.25 wt %, less than 0.1 wt %, less than 0.05 wt %, or less than 0.01 wt %. In another embodiment, the cyclic sulfur trioxide adduct composition comprises less than 1 wt % methyl-bis-chlorosulfate, e.g., less than 0.75 wt %, less than 0.5 wt %, less than 0.25 wt %, less than 0.1 wt %, less than 0.05 wt %, or less than 0.01 wt %. In another embodiment, the cyclic sulfur trioxide adduct composition comprises both chloromethyl chlorosulfate and methyl-bis-chlorosulfate, collectively, in an amount less than 1 wt %, e.g., less than 0.75 wt %, less than 0.5 wt %, less than 0.25 wt %, less than 0.1 wt %, less than 0.05 wt %, or less than 0.01 wt %.

In one embodiment, only the cyclizing agent (e.g., without solvent) is cooled, and then the cooled cyclizing agent is mixed with the solvent to form the cyclizing agent composition, which is then reacted with the acetoacetamide salt. That is, in some cases, the solvent (if present) may not be cooled in the same manner as the cyclizing agent is cooled. In other embodiments, only the solvent (without cyclizing agent) is cooled, and then the cooled solvent is mixed with the cyclizing agent to form the cyclizing agent composition. In some aspects both the solvent and the cyclizing agent are cooled prior to being mixed together to form the cyclizing agent composition. Regardless of whether either or both the solvent and the cyclizing agent are cooled prior to mixing, the resulting cyclizing agent composition optionally is further cooled.

Thus, in some cases, the cooling is implemented via multiple cooling steps. For example, the solvent may be cooled to a first temperature, then combined with the cyclizing agent to form the cyclizing agent composition, which is then further cooled to a second temperature, which is less than the first temperature. Conversely, in other aspects, the cyclizing agent is cooled to a first temperature, then combined with the solvent to form the cyclizing agent composition, which is then further cooled to a second temperature, which is less than the first temperature. In other embodiments, the cyclizing agent is cooled to a first temperature, the solvent is cooled to a second temperature, and the cooled cyclizing agent and the cooled solvent are combined and optionally cooled to a third temperature, which is less than the first and second temperatures. These cooling schemes are merely exemplary and are not intended to limit the scope of the cooling step.

In one embodiment, the solvent and cyclizing agent are combined in a first vessel, e.g., a first reactor, to form a cyclizing agent composition, which is optionally cooled. The cyclizing agent composition may then be added to the acetoacetamide salt in a second reactor. In one embodiment, the first vessel is chilled, e.g., to temperature below 35° C., prior to combining the solvent and cyclizing agent. In some aspects, the cyclizing agent and the solvent are cooled individually and then fed to the reaction with the acetoacetamide salt, optionally followed by additional cooling.

In addition to the aforementioned cooling steps, it has also been discovered that, in cases where the cyclizing agent and solvent are combined prior to reaction with the acetoacetamide salt, the formation of 5-chloro-acesulfame potassium may be advantageously further reduced or eliminated by reducing the contact time of the cyclizing agent and solvent. Thus, reducing the contact time optionally may be combined with any of the above-described cooling steps. The inventors have found that by limiting the contact time, less cyclizing agent/solvent reaction products, e.g., chlorosulfates such as chloromethyl chlorosulfate and methyl-bis-chlorosulfate, are beneficially formed. As a result, reductions in the formation of 5-chloro-acesulfame potassium may be achieved in the crude, intermediate, and finished acesulfame potassium compositions.

In some embodiments, for example, contact time may be less than 60 minutes, e.g., less than 45 minutes, less than 30 minutes, less than 15 minutes, less than 10 minutes, less than 8 minutes, less than 5 minutes, less than 3 minutes, or less than 1 minute. In one embodiment, the solvent and cyclizing agent are mixed and immediately reacted with the acetoacetamide salt. In terms of ranges, contact time may range from 1 second to 60 minutes, e.g., from 10 seconds to 45 minutes, from 10 seconds to 30 minutes, from 30 seconds to 30 minutes, from 1 minute to 10 minutes, from 3 minutes to 10 minutes, or from 5 minutes to 10 minutes. In preferred embodiments, as shown in the Examples, the combination of short contact times and low temperatures surprisingly leads to low 5-chloro-acesulfame potassium content in the crude, intermediate, and finished acesulfame potassium compositions.

The inventors have also found that if cyclization reaction time is minimized, the formation of impurities, e.g., organic impurities such as 5-chloro-acesulfame potassium, is reduced or eliminated. In some embodiments, the cyclization reaction is conducted for a cyclization reaction time less than 35 minutes, e.g., less than 30 minutes, less than 25 minutes, less than 20 minutes, less than 15 minutes, or less than 10 minutes. In terms of ranges, the cyclization reaction may be conducted for a cyclization reaction time ranging from 1 second to 35 minutes, e.g., from 10 seconds to 25 minutes, from 30 seconds to 15 minutes, or from 1 minute to 10 minutes.

Crude acesulfame compositions may be treated to form intermediate acesulfame potassium compositions and (subsequently) finished acesulfame potassium compositions The treatment operation may include one or more concentrating and/or separating operations.

For example, the treatment operation may comprise concentrating the crude acesulfame potassium composition to form a water stream and an intermediate acesulfame potassium composition and then separating the intermediate acesulfame potassium composition to form the finished acesulfame potassium composition comprising acesulfame potassium, e.g., via filtration and/or crystallization.

Acesulfame Potassium Compositions

The crude acesulfame potassium composition is formed by hydrolyzing the cyclic sulfur trioxide adduct to form an acesulfame-H composition and neutralizing the acesulfame-H in the acesulfame-H composition to form the crude acesulfame potassium composition, as discussed herein. The product of the neutralization reaction may be phase separated into aqueous and organic phases, and the crude acesulfame potassium composition may be obtained from the aqueous phase (without any further purification). The crude acesulfame potassium composition preferably comprises non-chlorinated acesulfame potassium, and less than 39 wppm 5-chloro-acesulfame potassium, e.g., less than 35 wppm, less than 34 wppm, less than 33 wppm, less than 32 wppm, less than 31 wppm, less than 30 wppm, less than 25 wppm, less than 24 wppm, less than 20 wppm, less than 15 wppm, less than 12 wppm, less than 10 wppm, less than 7 wppm, less than 5 wppm, less than 3 wppm, or less than 1 wppm. In some cases the crude acesulfame potassium composition is free of 5-chloro-acesulfame potassium, e.g., substantially free of 5-chloro-acesulfame potassium (undetectable). In terms of ranges, the crude acesulfame potassium composition may comprise from 1 wppb to 39 wppm 5-chloro-acesulfame potassium, e.g., from 1 wppb to 35 wppm, from 1 wppb to 34 wppm, from 1 wppb to 33 wppm, from 1 wppb to 32 wppm, from 1 wppb to 31 wppm, from 1 wppb to 30 wppm, from 50 wppb to 34 wppm, from 0.1 wppm to 34 wppm, from 0.1 wppb to 34 wppm, from 0.1 wppb to 33 wppm, from 1 wppb to 25 wppm, from 1 wppb to 20 wppm, from 1 wppb to 10 wppm, from 1 wppb to 5 wppm, from 1 wppb to 2.7 wppm, from 10 wppb to 20 wppm, from 10 wppb to 19 wppm, from 10 wppb to 15 wppm, from 10 wppb to 12 wppm, from 10 wppb to 10 wppm, from 10 wppb to 5 wppm, from 100 wppb to 15 wppm, from 100 wppb to 10 wppm, or from 100 wppb to 5 wppm.

The finished acesulfame potassium compositions, which are typically suitable for end consumer usage, are formed by treating the crude acesulfame potassium composition to remove impurities, as discussed herein. This finished acesulfame potassium composition preferably comprises non-chlorinated acesulfame potassium, e.g., non-chlorinated acesulfame potassium, and less than 39 wppm 5-chloro-acesulfame potassium, e.g., less than 35 wppm, less than 34 wppm, less than 33 wppm, less than 32 wppm, less than 31 wppm, less than 30 wppm, less than 25 wppm, less than 24 wppm, less than 20 wppm, less than 15 wppm, less than 12 wppm, less than 10 wppm, less than 7 wppm, less than 5 wppm, less than 3 wppm, or less than 1 wppm. In some cases the finished acesulfame potassium composition is free of 5-chloro-acesulfame potassium, e.g., substantially free of 5-chloro-acesulfame potassium (undetectable). In terms of ranges, the finished acesulfame potassium composition may comprise from 1 wppb to 39 wppm 5-chloro-acesulfame potassium, e.g., from 1 wppb to 35 wppm, from 1 wppb to 34 wppm, from 1 wppb to 33 wppm, from 1 wppb to 32 wppm, from 1 wppb to 31 wppm, from 1 wppb to 30 wppm, from 50 wppb to 34 wppm, from 0.1 wppm to 34 wppm, from 0.1 wppb to 34 wppm, from 0.1 wppb to 33 wppm, from 1 wppb to 25 wppm, from 1 wppb to 20 wppm, from 1 wppb to 10 wppm, from 1 wppb to 5 wppm, from 1 wppb to 2.7 wppm, from 10 wppb to 20 wppm, from 10 wppb to 19 wppm, from 10 wppb to 15 wppm, from 10 wppb to 12 wppm, from 10 wppb to 10 wppm, from 10 wppb to 5 wppm, from 100 wppb to 15 wppm, from 100 wppb to 10 wppm, or from 100 wppb to 5 wppm. The lower temperatures of the cyclizing agent composition (and optionally the shorter contact times) reduce or eliminate 5-chloro-acesulfame potassium formation, resulting in both a crude acesulfame potassium composition and a finished acesulfame potassium composition having low 5-chloro-acesulfame potassium content.

In some embodiments, the finished acesulfame potassium compositions comprise acesulfame potassium and less than 33 wppm acetoacetamide, e.g., less than 32 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the finished acesulfame potassium composition is free of acetoacetamide, e.g., substantially free of acetoacetamide (undetectable). In terms of ranges, the finished acesulfame potassium composition may comprise from 1 wppb to 33 wppm acetoacetamide, e.g., from 10 wppb to 32 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm. In some cases, acetoacetamide-N-sulfonic acid may also be present in the finished acesulfame potassium compositions in the aforementioned amounts. These impurities may be formed by side reactions and degradation of the acesulfame potassium and acesulfame-H molecules, e.g., during treatment of the specific crude acesulfame potassium compositions discussed herein.

The 5-chloro-acesulfame potassium content may be measured in the crude and/or finished acesulfame potassium compositions (as well as any intermediate compositions) via high performance liquid chromatography (HPLC) analysis, based on European Pharmacopoeia guidelines (2017), based on European Pharmacopoeia guidelines for thin layer chromatography (2017) and adapted for HPLC. A particular measurement scenario utilizes an LC Systems HPLC unit from Shimadzu having a CBM-20 Shimadzu controller and being equipped with a CC 250/4.6 Nucleodur 100-3 C18 ec (250×4.6 mm) MACHEREY NAGEL column. A Shimadzu SPD-M20A photodiode array detector can be used for detection (at 234 nm wavelength). Analysis may be performed at 23° C. column temperature. As an eluent solution, an aqueous solution of tetra butyl ammonium hydrogen sulfate (optionally at 3.4 g/L and at 60% of the total solution) and acetonitrile (optionally at 300 mL/L and at 40% of the total solution) may be employed. Elution may be isocratic. The overall flow rate of total eluent may be approximately 1 mL/min. The data collection and calculations may be performed using Lab Solution software from Shimadzu.

The acetoacetamide-N-sulfonic acid and/or the acetoacetamide content may be measured in the crude, intermediate, or finished acesulfame potassium compositions via HPLC analysis, based on European Pharmacopoeia guidelines for thin layer chromatography (2017) and adapted for HPLC. A particular measurement scenario utilizes an LC Systems HPLC unit from Shimadzu having a CBM-20 Shimadzu controller and being equipped with an IonPac NS1 ((5 µm) 150×4 mm) analytical column and an IonPac NG1 guard column (35×4.0 mm). A Shimadzu SPD-M20A photodiode array detector can be used for detection (at 270 nm and 280 nm wavelength). Analysis may be performed at 23° C. column temperature. As a first eluent solution, an aqueous mixture of tetra butyl ammonium hydrogen sulfate (3.4 g/L), acetonitrile (300 mL/L), and potassium hydroxide (0.89 g/L) may be employed; as a second eluent solution, an aqueous mixture of tetra butyl ammonium hydrogen sulfate (3.4 g/L) and potassium hydroxide (0.89 g/L) may be employed. Elution may be conducted in gradient mode according to the following second eluent flow profile:

0 to 3 minutes: constant 80% (v/v)
3 to 6 minutes: linear reduction to 50% (v/v)
6 to 15 minutes: constant at 50% (v/v)
15 to 18 minutes: linear reduction to 0%
18 to 22 minutes: constant at 0%
22 to 24 minutes: linear increase to 80% (v/v)
24 to 35 minutes constant at 80% (v/v).

Overall flow rate of eluent may be approximately 1.2 mL/min. The data collection and calculations may be performed using Lab Solution software from Shimadzu.

As noted above, the crude acesulfame potassium composition is formed by the aforementioned cooling of the cyclizing agent composition/provision of a cooled cyclizing agent composition, cyclic sulfur trioxide adduct composition formation reaction, hydrolysis, and neutralization steps and the finished acesulfame potassium composition is formed by treatment of the crude acesulfame potassium composition. In preferred embodiments, the cooled cyclizing agent composition may have a temperature less than 35° C., e.g., e.g., less than 32° C., less than 30° C., less than 25° C., less than 20° C., less than 15° C., less than 12° C., less than 11° C., less than 10° C., less than 8° C., less than 5° C., less than 3° C., less than 1° C., or less than 0° C. (optionally a temperature ranging from −45° C. to 35° C., e.g., −45° C. to 25° C., −40° C. to 15° C., −35° C. to 15° C., −35° C. to 10° C., −30° C. to 25° C., −30° C. to 10° C., −15° C. to 25° C., from −15° C. to 15° C., from −10° C. to 12° C., from −8° C. to 10° C., or −8° C. to 5° C.); the contact time may be less than 60 minutes, e.g., less than 45 minutes, less than 30 minutes, less than 15 minutes, less than 10 minutes, less than 8 minutes, less than 5 minutes, less than 3 minutes, or less than 1 minute (optionally ranging from 1 second to 60 minutes, e.g., from 1 second to 45 minutes, from 1 second to 30 minutes, from 1 second to 15 minutes, from 1 second to 10 minutes, from 1 minute to 45 minutes, from 1 minute to 30 minutes, from 1 minute to 15 minutes, from 1 minute to 10 minutes, from 10 seconds to 45 minutes, from 10 seconds to 30 minutes, from 30 seconds to 30 minutes, from 1 minute to 10 minutes, from 3 minutes to 10 minutes, or from 5 minutes to 10 minutes); the crude acesulfame potassium composition may comprise from 1 wppb to 39 wppm 5-chloro-acesulfame potassium, e.g., from 1 wppb to 35 wppm, from 1 wppb to 34 wppm, from 1 wppb to 33 wppm, from 1 wppb to 32 wppm, from 1 wppb to 31 wppm, from 1 wppb to 30 wppm, from 50 wppb to 34 wppm, from 0.1 wppm to 34 wppm, from 0.1 wppb to 34 wppm, from 0.1 wppb to 33 wppm, from 1 wppb to 25 wppm, from 1 wppb to 20 wppm, from 1 wppb to 10 wppm, from 1 wppb to 5 wppm, from 1 wppb to 2.7 wppm, from 10 wppb to 20 wppm, from 10 wppb to 19 wppm, from 10 wppb to 15 wppm, from 10 wppb to 12 wppm, from 10 wppb to 10 wppm, from 10 wppb to 5 wppm, from 100 wppb to 15 wppm, from 100 wppb to 10 wppm, or from 100 wppb to 5 wppm (optionally less than 35 wppm, less than 34 wppm, less than 33 wppm, less than 32 wppm, less than 31 wppm, less than 30 wppm, less than 25 wppm, less than 24 wppm, less than 20 wppm, less than 15 wppm, less than 12 wppm, less than 10 wppm, less than 7 wppm, less than 5 wppm, less than 3 wppm, or less than 1 wppm); and the finished acesulfame potassium composition may comprise from 1 wppb to 39 wppm 5-chloro-acesulfame potassium, e.g., from 1 wppb to 35 wppm, from 1 wppb to 34 wppm, from 1 wppb to 33 wppm, from 1 wppb to 32 wppm, from 1 wppb to 31 wppm, from 1 wppb to 30 wppm, from 50 wppb to 34 wppm, from 0.1 wppm to 34 wppm, from 0.1 wppb to 34 wppm, from 0.1 wppb to 33 wppm, from 1 wppb to 25 wppm, from 1 wppb to 20 wppm, from 1 wppb to 10 wppm, from 1 wppb to 5 wppm, from 1 wppb to 2.7 wppm, from 10 wppb to 20 wppm, from 10 wppb to 19 wppm, from 10 wppb to 15 wppm, from 10 wppb to 12 wppm, from 10 wppb to 10 wppm, from 10 wppb to 5 wppm, from 100 wppb to 15 wppm, from 100 wppb to 10 wppm, or from 100 wppb to 5 wppm (optionally less than 39 wppm 5-chloro-acesulfame potassium, e.g., less than 35 wppm, less than 34 wppm, less than 33 wppm, less than 32 wppm, less than 31 wppm, less than 30 wppm, less than 25 wppm, less than 24 wppm, less than 20 wppm, less than 15 wppm, less than 12 wppm, less than 10 wppm, less than 7 wppm, less than 5 wppm, less than 3 wppm, or less than 1 wppm).

In a particular embodiment, the cooled cyclizing agent composition has a cooled temperature less than 25° C., the crude acesulfame potassium composition comprises from 1 wppb to 39 wppm 5-chloro-acesulfame potassium, the finished acesulfame potassium composition comprises from 1 wppb to 5 wppm 5-chloro-acesulfame potassium.

In another particular embodiment, the cooled cyclizing agent composition has a cooled temperature ranging from −35° C. to 15° C., the crude acesulfame potassium composition comprises from 1 wppb to 5 wppm 5-chloro-acesulfame potassium, the finished acesulfame potassium composition comprises from 1 wppb to 2.7 wppm 5-chloro-acesulfame potassium.

In another particular embodiment, the cooled cyclizing agent composition has a cooled temperature less than 25° C., the contact time is less than 15 minutes, the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium.

In another particular embodiment, the cooled cyclizing agent composition has a cooled temperature ranging from −35° C. to 15° C., the contact time is less than 5 minutes, the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium.

In another particular embodiment, the cooled cyclizing agent composition has a cooled temperature less than 25° C., the contact time is less than 5 minutes, the crude acesulfame potassium composition comprises from 1 wppb to 39 wppm 5-chloro-acesulfame potassium, and the finished acesulfame potassium composition comprises from 1 wppb to 5 wppm 5-chloro-acesulfame potassium.

The acesulfame potassium compositions (crude and/or finished) may, in some cases, comprise other impurities. Exemplary impurities include, inter alia, acetoacetamide, acetoacetamidesulfonate, and acetoacetamide-N-sulfonic acid. The acesulfame potassium compositions (crude and/or finished) also may comprise heavy metals. The organic impurities and/or heavy metals may be present in an amount ranging from 1 wppb to 25 wppm, based on the total weight of the respective acesulfame potassium composition, crude or finished, e.g., from 100 wppb to 20 wppm, from 100 wppb to 15 wppm, from 500 wppb to 10 wppm, or from 1 wppm to 5 wppm. Heavy metals are defined as metals with relatively high densities, e.g., greater than 3 g/cm$^3$ or greater than 7 g/cm$^3$. Exemplary heavy metals include lead and mercury. In some cases, the crude or finished acesulfame potassium composition may comprise mercury in an amount ranging from 1 wppb to 25 wppm, e.g., from 100 wppb to 20 wppm, from 100 wppb to 15 wppm, from 500 wppb to 10 wppm, or from 1 wppm to 5 wppm. In terms of limits, the crude or finished acesulfame potassium composition may comprise less than 25 wppm mercury, e.g., less than 20 wppm, less than 15 wppm, less than 10 wppm, or less than 5 wppm. In some cases, the crude or finished acesulfame potassium composition may comprise lead in an amount ranging from 1 wppb to 25 wppm, e.g., from 100 wppb to 20 wppm, from 100 wppb to 15 wppm, from 500 wppb to 10 wppm, or from 1 wppm to 5 wppm. In terms of limits, the crude or finished acesulfame potassium composition may comprise less than 25 wppm lead, e.g., less than 20 wppm, less than 15 wppm, less than 10 wppm, or less than 5 wppm. In some cases, when potassium hydroxide is formed via a membrane process, the resultant crude or finished acesulfame potassium composition may have very low levels of mercury, if any, e.g., less than 10 wppm, less than 5 wppm, less than 3 wppm, less than 1 wppm, less than 500 wppb, or less than 100 wppb.

In some embodiments, the acesulfame potassium compositions (crude, intermediate, and/or finished) may comprise acetoacetamide-N-sulfonic acid, e.g., less than 37 wppm acetoacetamide-N-sulfonic acid, e.g., less than 35 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the finished acesulfame potassium composition is substantially free of acetoacetamide-N-sulfonic acid, e.g., free of acetoacetamide-N-sulfonic acid. In terms of ranges, the finished acesulfame potassium composition may comprise from 1 wppb to 37 wppm acetoacetamide-N-sulfonic acid, e.g., from 10 wppb to 35 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm. Acetoacetamide-N-sulfonic acid may be formed in side reactions. The use of the aforementioned temperature (and optionally contact time) parameters also provide for low amounts of acetoacetamide-N-sulfonic acid.

In some embodiments, the crude acesulfame potassium composition is treated to achieve the finished acesulfame potassium composition. In some cases, however, treatment steps may not provide for removal of 5-chloro-acesulfame potassium, perhaps due to the chemical similarities of 5-chloro-acesulfame potassium and acesulfame potassium. Surprisingly, the use of the process steps disclosed herein advantageously provides for the reduction or elimination of impurities during the reaction scheme, before purification of the crude acesulfame potassium composition. Accordingly, the need to rely on purification of the crude acesulfame potassium composition to remove 5-chloro-acesulfame potassium is beneficially reduced. In some embodiments, the acesulfame potassium compositions (crude and/or finished) comprise at least 90% of the 5-chloro-acesulfame potassium present the crude acesulfame potassium composition, e.g., at least 93%, at least 95%, or at least 99%.

Intermediate Reaction Parameters

The reactions for production of high purity acesulfame potassium are described in more detail as follows.

Amidosulfamic Acid Salt Formation Reaction

In a first reaction step, sulfamic acid and an amine are reacted to form sulfamic acid salt. An exemplary reaction scheme that employs triethylamine as the amine and yields triethyl ammonium sulfamic acid salt is shown in reaction (1), below.

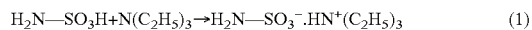

$$H_2N-SO_3H + N(C_2H_5)_3 \rightarrow H_2N-SO_3^- \cdot HN^+(C_2H_5)_3 \quad (1)$$

Acetic acid is also present in the first reaction mixture and reacts with the amine, e.g., triethylamine, to form an ammonium acetate, e.g., triethylammonium acetate, as shown in reaction (2), below.

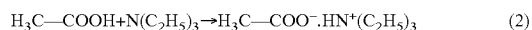

$$H_3C-COOH + N(C_2H_5)_3 \rightarrow H_3C-COO^- \cdot HN^+(C_2H_5)_3 \quad (2)$$

The amine employed in these reactions may vary widely. Preferably, the amine comprises triethylamine. In one embodiment, the amine may be selected from the group consisting of trimethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine, triisopropylentriamine, and mixtures thereof.

Acetoacetamide Salt Formation Reaction

Once formed in reaction (1), the sulfamic acid salt is reacted with the acetoacetylating agent to form the acetoacetamide salt, preferably acetoacetamide-N-sulfonate triethylammonium salt. Preferably, the acetoacetylating agent comprises diketene, although other acetoacetylating agents may be employed, either with or without diketene.

In one embodiment, the resultant acetoacetamide salt corresponds to the following formula (3).

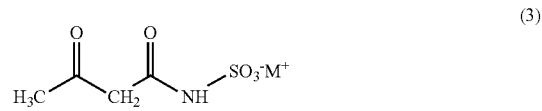

(3)

wherein M$^+$ is an appropriate ion. Preferably, M$^+$ is an alkali metal ion or N$^+$R$_1$R$_2$R$_3$R$_4$. R$_1$, R$_2$, R$_3$ and R$_4$, independently of one another, may be organic radicals or hydrogen, preferably H or $C_1$-$C_8$ alkyl, $C_6$-$C_{10}$ cycloalkyl, aryl and/or aralkyl. In a preferred embodiment, $R_1$ is hydrogen, and $R_2$, $R_3$ and $R_4$ are alkyl, e.g., ethyl.

An exemplary reaction scheme for forming an acetoacetamide salt employs a trialkyl ammonium amidosulfamic acid salt and diketene as reactants and yields an acetoacetamide triethylammonium salt is shown in reaction (4), below.

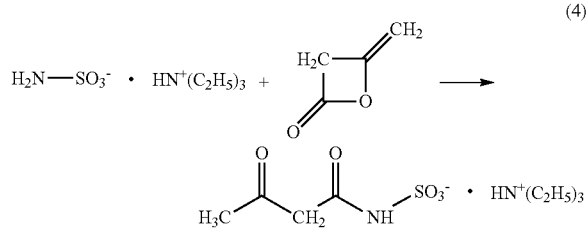

In one embodiment, the reaction is conducted in the presence of a catalyst, which may vary widely. In some embodiments, the catalyst comprises one or more amines and/or phosphines. Preferably, the catalyst comprises triethylamine. In some cases trimethylamine serves as both a catalyst and a reactant.

In one embodiment wherein the amidosulfamic acid salt formation reaction and the acetoacetamide salt formation reaction are conducted in separate reactors, a second reaction mixture comprises the amidosulfamic acid salt, the diketene, and the catalyst, e.g., triethylamine. Preferably, catalyst from the first reaction is carried through to the reaction mixture of the second reaction. The second reaction mixture is then subjected to conditions effective to form the acetoacetamide salt.

In one embodiment, the composition of the second reaction mixture may be similar to that of the first reaction mixture. In a preferred embodiment, the reaction product of the amidosulfamic acid salt formation reaction provides the amidosulfamic acid salt component of the second reaction mixture. In addition to the above-mentioned components, the second reaction mixture may further comprise reaction by-products from the first reaction or non-reacted starting materials.

In one embodiment, the amount of acetoacetylating agent, e.g., diketene, should be at least equimolar to the reactant amidosulfamic acid salt that is provided. In one embodiment, the process may utilize a diketene in excess, but preferably in an excess less than 30 mol %, e.g., less than 10 mol %. Greater excesses are also contemplated.

The amidosulfamic acid salt formation reaction and/or the acetoacetamide salt formation reaction may employ an organic solvent. Suitable inert organic solvents include any organic solvents that do not react in an undesired manner with the starting materials, cyclizing agent, final products and/or the catalysts in the reaction. The solvents preferably have the ability to dissolve, at least partially, amidosulfamic acid salts. Exemplary organic solvents include halogenated aliphatic hydrocarbons, preferably having up to 4 carbon atoms such as, for example, methylene chloride, chloroform, 1,2-dichlorethane, trichloroethylene, tetrachloroethylene, trichlorofluoroethylene; aliphatic ketones, preferably those having 3 to 6 carbon atoms such as, for example, acetone, methyl ethyl ketone; aliphatic ethers, preferably cyclic aliphatic ethers having 4 or 5 carbon atoms such as, for example, tetrahydrofuran, dioxane; lower aliphatic carboxylic acids, preferably those having 2 to 6 carbon atoms such as, for example, acetic acid, propionic acid; aliphatic nitriles, preferably acetonitrile; N-alkyl-substituted amides of carbonic acid and lower aliphatic carboxylic acids, preferably amides having up to 5 carbon atoms such as, for example, tetramethylurea, dimethylformamide, dimethylacetamide, N-methylpyrrolidone; aliphatic sulfoxides, preferably dimethyl sulfoxide, and aliphatic sulfones, preferably sulfolane.

Particularly preferred solvents include dichloromethane (methylene chloride), 1,2-dichloroethane, acetone, glacial acetic acid and dimethylformamide, with dichloromethane (methylene chloride) being particularly preferred. The solvents may be used either alone or in a mixture. In one embodiment, the solvent is a halogenated, aliphatic hydrocarbon solvent, preferably the solvent is dichloromethane. Chloroform and tetrachloromethane are also exemplary solvents.

In one embodiment, the acetoacetamide salt formation reaction is conducted a temperature ranging from −30° C. to 50° C., e.g., from 0° C. to 25° C. The reaction pressure may vary widely. In preferred embodiments, the reaction is carried out at atmospheric pressure, although other pressures are also contemplated. The reaction time may vary widely, preferably ranging from 0.5 hours to 12 hours, e.g., from 1 hour to 10 hours. In one embodiment, the reaction is carried out by introducing the amidosulfamic acid salt and metering in the diketene. In another embodiment, the reaction is carried out by introducing diketene and metering in the amidosulfamic acid salt. The reaction may be carried out by introducing the diketene and amidosulfamic acid and metering in the catalyst.

Once formed, each reaction product is optionally subjected to one or more purification steps. For example, the solvent may be separated from the reaction product, e.g., via distillation, and the residue (mainly acetoacetamide-N-sulfonate) may be recrystallized from a suitable solvent such as, for example, acetone, methyl acetate or ethanol.

Generally speaking, the steps of reacting the sulfamic acid and triethylamine to form an amidosulfamic acid salt, reacting the amidosulfamic acid salt and diketene to form acetoacetamide salt, providing the cyclizing agent composition, and cooling the cyclizing agent composition, may be performed in any order before the cyclization reaction, e.g., the reaction of the acetoacetamide salt with sulfur trioxide to form a cyclic sulfur trioxide adduct. Each of these steps may be performed independently of one another. In some cases, these steps may be performed in any order as long as they are performed before the cyclization reaction, e.g., the reaction of the acetoacetamide salt with sulfur trioxide to form a cyclic sulfur trioxide adduct.

Cyclization and Hydrolyzation

As discussed above, the acetoacetamide salt is reacted with cyclizing agent, e.g., cyclizing agent in the cooled cyclizing agent composition, in the presence of a solvent to form the cyclic (sulfur trioxide) adduct composition, which contains cyclic sulfur trioxide adduct and, in some cases, impurities. As discussed, a cooling step occurs before the cyclic sulfur trioxide adduct formation reaction. In one embodiment, the cyclization is achieved by using at least an equimolar amount of the cyclizing agent. The cyclizing agent may be dissolved in an inert inorganic or organic solvent. The cyclizing agent is generally used in a molar excess, e.g., up to a 20 fold excess, or up to a 10 fold excess, based on the total moles of acetoacetamide salt. An exemplary cyclization reaction using sulfur trioxide as the cyclizing agent is shown in reaction (5), below.

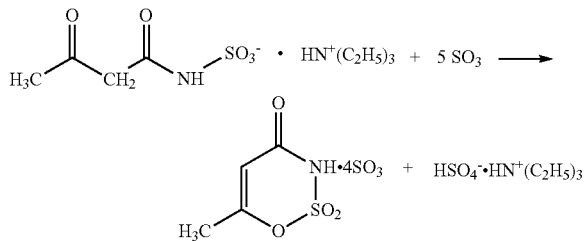

(5)

In one embodiment, the weight ratio of solvent to cyclizing agent in the cyclizing agent composition is at least 1:1, e.g., at least 2:1, or at least 5:1. In one embodiment, the weight ratio of solvent to cyclizing agent in the cyclizing agent composition ranges from 1:1 to 25:1, e.g., from 1:1 to 10:1, from 2:1 to 10:1, or from 5:1 to 10:1.

A cyclizing agent may be any compound that initiates the ring closure of the acetoacetamide salt. Although sulfur trioxide is a preferred cyclizing agent, the employment of other cyclizing agents is contemplated.

Suitable inert inorganic or organic solvents are those liquids which do not react in an undesired manner with sulfur trioxide or the starting materials or final products of the reaction. Preferred organic solvents include, but are not limited to, halogenated aliphatic hydrocarbons, preferably having up to four carbon atoms, such as, for example, methylene chloride (dichloromethane), chloroform, 1,2-dichloroethane, trichloroethylene, tetrachloroethylene, trichlorofluoroethylene; esters of carbonic acid with lower aliphatic alcohols, preferably with methanol or ethanol; nitroalkanes, preferably having up to four carbon atoms, in particular nitromethane; alkyl-substituted pyridines, preferably collidine; and aliphatic sulfones, preferably sulfolane. Particularly preferred solvents for the cyclization reaction include dichloromethane (methylene chloride), 1,2-dichloroethane, acetone, glacial acetic acid and dimethylformamide, with dichloromethane (methylene dichloride) being particularly preferred. Other solvents, e.g., other solvents mentioned herein, may also be suitable as solvents. The solvents may be used either alone or in a mixture. In one embodiment, the solvent is a halogenated, aliphatic hydrocarbon solvent, preferably the solvent is dichloromethane. The processes may employ these solvents alone or in mixtures thereof.

In some cases, the solvent in the cyclizing agent composition may be selected from 1) concentrated sulfuric acid, 2) liquid sulfur dioxide, or 3) an inert organic solvent.

In a preferred embodiment, the same solvent is used in both the acetoacetamide salt formation reaction and the cyclization reaction. As one benefit, the solution obtained in the acetoacetamide salt formation reaction, without isolation of the acetoacetamide salt formation reaction product, may be used immediately in the cyclization.

The pressure at which the reaction is conducted may vary widely. In one embodiment, the reaction is conducted at a pressure ranging from 0.01 MPa to 10 MPa, e.g., from 0.1 MPa to 5 MPa. Preferably, the reaction is conducted at atmospheric pressure.

The acetoacetamide salt may be introduced to the cyclization reactor and the cooled cyclizing agent composition, e.g., a solution of cyclizing agent optionally in solvent, may be metered into the reactor. In preferred embodiments, both reactants (acetoacetamide salt and cyclizing agent) are simultaneously fed into the reactor. In one embodiment, the cooled cyclizing agent composition is initially introduced into the reactor and the acetoacetamide salt is added. Preferably, at least part of the cyclizing agent composition is introduced into the reactor and, either continuously or in portions, acetoacetamide salt and (additional) cyclizing agent are then metered in, preferably while maintaining the temperature as described above.

The acetoacetamide salt may be introduced to the reactor and the cyclizing agent composition may be metered into the reactor. In preferred embodiments, both reactants are simultaneously fed into the reactor. In one embodiment, the cyclizing agent composition is initially introduced into the reactor and the acetoacetamide salt is added. Preferably, at least part of the cyclizing agent composition is introduced into the reactor and, either continuously or in portions, acetoacetamide salt and (additional) cyclizing agent are then metered in, preferably while maintaining the temperature as described above.

The formation of the crude acesulfame potassium composition from the cyclic sulfur trioxide adduct composition, in some embodiments, comprises the steps of hydrolyzing the cyclic sulfur trioxide adduct to form an acesulfame-H composition; neutralizing the acesulfame-H in the acesulfame H composition to form a crude acesulfame potassium composition; and forming the acesulfame potassium composition from the crude acesulfame potassium composition.

The cyclic sulfur trioxide adduct may be hydrolyzed via conventional means, e.g., using water. Thus, the forming step may comprise the steps of hydrolyzing the cyclic sulfur trioxide adduct to form an acesulfame-H composition. Acesulfame-H is referred to as sweetener acid.

An exemplary hydrolysis reaction scheme is shown in reaction (6), below.

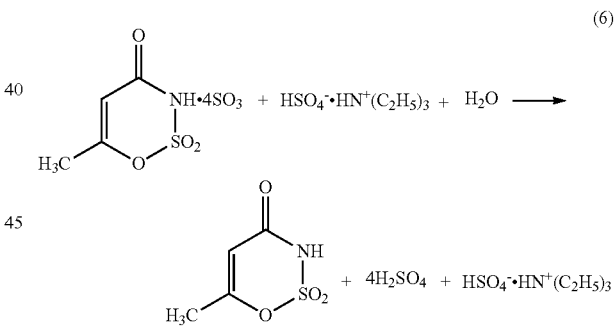

(6)

The addition of the water leads to a phase separation. The majority of the sweetener acid, acesulfame-H (6-methyl-3,4-dihydro-1,2,3-oxathiazin-4-one 2,2-dioxide), which is formed via the hydrolysis, is present in the organic phase, e.g., at least 60 wt %, at least 70%, at least 80%, or at least 90%. The remainder of the sweetener acid is in the water phase and can be extracted and optionally added to the sweetener acid in the organic phase. In cases where dichloromethane is used as the reaction medium, water or ice may be added, e.g., in a molar excess, based on the sulfur trioxide, to the cyclic sulfur trioxide adduct/sulfur trioxide solution.

In some cases, the hydrolysis step comprises adding water to the cyclic sulfur trioxide adduct. In preferred embodiments, the weight ratio of water to acetoacetamide salt is greater than 1.3:1, e.g., greater than 1.5:1, greater than 1.7:1, greater than 2:1 or greater than 2.2:1. Employment of these ratios may lead to decreases in acetoacetamide-N-sulfonic acid and/or acetoacetamide formation in the neutralized crude acesulfame potassium composition, e.g., the crude acesulfame potassium composition may comprise acetoacetamide-N-sulfonic acid in the amounts discussed herein.

It was surprisingly discovered that the temperature at which the water is initially fed to the hydrolysis reaction may have beneficial effects on impurity production, e.g., organic production or 5-chloro-acesulfame potassium production as well as reaction parameters, e.g., temperature. At lower temperatures, e.g., lower than approximately −35° C. or lower than −22° C., ice tends to build up in the reaction mixture. As this ice melted, it led to the onset of additional reaction, which caused the temperature to rise quickly. This rise in temperature surprisingly led to a product that contained much higher levels of impurities. In some cases, the hydrolyzing comprises adding hydrolysis water to the cyclic sulfur trioxide adduct to form a hydrolysis reaction mixture and reacting the mixture to from the acesulfame-H composition. In some embodiments, the temperature of the hydrolysis reaction mixture or the temperature at which the hydrolysis water is fed to the reactor is maintained at a temperature greater than −35° C., e.g., greater than −30° C., greater than −25° C., greater than −24° C., greater than −23° C., greater than −22° C., greater than −21.5° C., greater than −21° C., or greater than greater than −20° C. In terms of ranges, the temperature of the hydrolysis reaction mixture or the temperature at which the hydrolysis water is fed to the reactor optionally is maintained at a temperature ranging from −35° C. to 0° C., e.g., from −30° C. to −5° C., from −20° C. to −5° C., from −30° C. to −20° C., from −25° C. to −21° C., or −25° C. to −21.5° C.

After the addition of water, the reaction solvent, e.g., dichloromethane, may be removed by distillation, or the acesulfame-H that remains in the organic phase may be extracted with a more suitable solvent. Suitable solvents are those which are sufficiently stable towards sulfuric acid and which have a satisfactory dissolving capacity. Other suitable solvents include esters of carbonic acid such as, for example dimethyl carbonate, diethyl carbonate and ethylene carbonate, or esters of organic monocarboxylic acids such as, for example, isopropyl formate and isobutyl formate, ethyl acetate, isopropyl acetate, butyl acetate, isobutyl acetate and neopentyl acetate, or esters of dicarboxylic acids or amides which are immiscible with water, such as, for example, tetrabutylurea, are suitable. Isopropyl acetate and isobutyl acetate are particularly preferred.

The combined organic phases are dried with, for example, $Na_2SO_4$, and are evaporated. Any sulfuric acid which has been carried over in the extraction may be removed by appropriate addition of aqueous alkali to the organic phase. For this purpose, dilute aqueous alkali may be added to the organic phase until the pH reached in the aqueous phase corresponds to that of pure 6-methyl-3,4-dihydro-1,2,3-oxathiazin-4-one 2,2-dioxide at the same concentration in the same two-phase system of extracting agent and water.

Neutralization

The neutralization of the acesulfame-H yields a non-toxic salt of acesulfame-H, e.g., acesulfame potassium. In one embodiment, neutralization is carried out by reacting the acesulfame-H with an appropriate base, e.g., potassium hydroxide, in particular a membrane-produced potassium hydroxide. Other suitable bases include, for example, KOH, $KHCO_3$, $K_2CO_3$, and potassium alcoholates. An exemplary reaction scheme using potassium hydroxide as a neutralizing agent is shown in reaction (7), below.

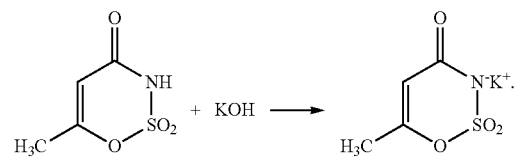

(7)

In some cases, the neutralization is conducted or maintained at a low pH levels, which may advantageously further result in a reduction or elimination of the formation of impurities, e.g., acetoacetamide salts. In this context, "conducted" means that the neutralization step begins at a low pH level, and "maintained" means that steps are taken to ensure that the pH stays within a low pH range throughout the entire neutralization step. In one embodiment, the neutralization step is conducted or maintained at a pH below 10.0, e.g., below 9.5, below 9.0, below 8.5, below 8.0, below 7.5, below 7.0, or below 6.5. In terms of ranges, the neutralization step is preferably conducted or maintained at a pH between 6.0 and 10.0, e.g., between 6.5 and 9.5, between 7.0 and 9.0, or between 7.5 and 8.5.

In some cases, the pH in the neutralizing step may be maintained within the desired range by managing the components of the neutralization reaction mixture, which comprises acesulfame-H and neutralizing agent (and also solvent). For example, the composition of the neutralization reaction mixture may include from 1 wt % to 95 wt % neutralizing agent, e.g., from 10 wt % to 85 wt % or from 25 wt % to 75 wt %, and from 1 wt % to 95 wt % acesulfame-H, e.g., from 10 wt % to 85 wt % or from 25 wt % to 75 wt %. These concentration ranges are based on the mixture of neutralization agent and acesulfame-H (not including solvent).

In one embodiment, the acesulfame-H may be neutralized and extracted directly from the purified organic extraction phase using an aqueous potassium base. The acesulfame potassium then precipitates out, where appropriate after evaporation of the solution, in the crystalline form, and it can also be recrystallized for purification.

In one embodiment, the process is not a small-scale batch process or a laboratory-scale process. For example, the inventive process for producing a finished acesulfame potassium composition may yield at least 50 grams of finished acesulfame potassium composition per batch, e.g., at least 100 grams per batch, at least 500 grams per batch, at least 1 kilogram per batch, or at least 10 kilograms per batch. In terms of rates, the inventive process may yield at least 50 grams of finished acesulfame potassium composition per hour, e.g., at least 100 grams per hour, at least 500 grams per hour, at least 1 kilogram per hour, or at least 10 kilograms per hour.

FIG. 1 shows an exemplary acesulfame potassium process 100 in accordance with the process described herein. Process 100 comprises amidosulfamic acid salt formation reactor 102 and acetoacetamide salt formation reactor 104. Although FIG. 1 shows separate reactors for the two intermediate formation reactions, other configurations, e.g., a one reactor process, are within the contemplation of the present process. Sulfamic acid is fed to amidosulfamic acid salt formation reactor 102 via sulfamic acid feed line 106. Amine(s), preferably triethylamine, are fed to amidosulfamic acid salt formation reactor 102 via amine feed line 108. In addition to sulfamic acid and amine(s), acetic acid is also fed to amidosulfamic acid salt formation reactor 102

(via feed line 110). The resultant reaction mixture in amidosulfamic acid salt formation reactor 102 is as discussed above. In amidosulfamic acid salt formation reactor 102, the sulfamic acid and the amine (in the presence of the acetic acid) are reacted to yield a crude amidosulfamic acid salt composition, which exits reactor 102 via line 112. Although not shown, a reaction solvent, e.g., dichloromethane may also be present in the amidosulfamic acid salt formation reactor 102.

The crude amidosulfamic acid salt composition in line 112 is directed to acetoacetamide salt formation reactor 104. Diketene is fed to acetoacetamide salt formation reactor 104 via feed line 114. In acetoacetamide salt formation reactor 104, the amidosulfamic acid salt and the diketene are reacted to yield a crude acetoacetamide salt composition, which exits reactor 104 via line 118. Although not shown, dichloromethane may also be present in the acetoacetamide salt formation reactor 104.

Cyclizing agent (sulfur dioxide) and solvent (dichloromethane) are fed to vessel 119 via feed lines 121 and 123. Vessel 119 is preferably a cooling vessel wherein the cyclizing agent composition (as discussed above) is formed. The cyclizing agent composition exits vessel 119 via line 125.

The crude acetoacetamide salt composition is directed to cyclization reactor 120 via line 118. The cooled cyclizing agent composition is also directed to cyclization reactor 120 (via line 125). Line 125 is preferably made of a material and in such a size and shape to facilitate the residence times discussed herein. In cyclization reactor 120, the acetoacetamide salt in the crude acetoacetamide salt composition in line 118 is cyclized and a cyclic sulfur trioxide adduct stream exits via line 124.

The cyclic sulfur trioxide adduct in line 124, is directed to hydrolysis reactor 126. Water is fed to hydrolysis reactor 126 via water feed 128. In hydrolysis reactor 126, the cyclic sulfur trioxide adduct is hydrolyzed to yield a crude acesulfame-H composition, which exits hydrolysis reactor 126 via line 130 and is directed to phase separation unit 132. Phase separation unit 132 separates the contents of line 130 into organic phase 134 and aqueous phase 136. Organic phase 134 comprises a major amount of the acesulfame-H in line 130 as well as solvent, e.g., methylene chloride. Aqueous phase 136 exits via line 137 and comprises triethylammonium sulfate, and optionally sulfuric acid and minor amounts of acesulfame-H. This aqueous phase may be further purified to separate and/or recover the acesulfame-H and/or the triethylammonium sulfate. The recovered acesulfame-H may be combined with the acesulfame from the organic phase (not shown).

Organic phase 134 exits phase separation unit 132 and is directed to extraction column 138 (via line 140). Water is fed to extraction column 138 via water feed 142. The water extracts residual sulfates from the contents of line 140 and a purified acesulfame-H composition exits extraction column 138 via line 144. The extracted sulfates exit extraction column 138 via line 145.

The purified acesulfame-H composition in line 144 is directed to neutralization unit 146. Potassium hydroxide is also fed to neutralization unit 146 (via line 148). The potassium hydroxide neutralizes the acesulfame-H in the purified acesulfame-H composition to yield a product comprising acesulfame potassium, dichloromethane, water, potassium hydroxide, and impurities, e.g., 5-chloro-acesulfame potassium, which exits neutralization unit 146 via line 150. This product may be considered a crude acesulfame potassium composition.

The product in line 150 is directed to phase separation unit 160. Phase separation unit 160 separates the product in line 150 into organic phase 162 and an aqueous phase 164. Aqueous phase 164 comprises a major amount of the acesulfame potassium in line 150 as well as some impurities. Organic phase 162 comprises potassium hydroxide, dichloromethane, and water and may be further treated to recover these components. Aqueous phase 164 (without any further treatment) may be considered a crude acesulfame potassium composition. Aqueous phase 164 may be optionally treated to form a finished acesulfame potassium composition.

Aqueous phase 164 is directed to treatment unit 156 via line 166. In treatment unit 156, aqueous phase 164 is treated to obtain finished acesulfame potassium composition (product that may be sold), which is shown exiting via stream 152. In addition to the finished acesulfame potassium composition, dichloromethane and potassium hydroxide may be separated. These components exit treatment unit 156 via line 154. The contents of stream 154 may be recovered and/or recycled to the process.

The crude acesulfame potassium product stream comprises acesulfame potassium, dichloromethane, water, and potassium hydroxide. The crude acesulfame potassium product stream in line 150 may be directed to further processing to recover purified acesulfame potassium, which is shown exiting via stream 152. In addition to the purified acesulfame potassium, dichloromethane and potassium hydroxide may be separated from the crude acesulfame potassium product stream, as shown by stream 154. The contents of stream 154 may be recovered and/or recycled to the process.

The invention relates also to the following aspects:

Aspect 1: A process for producing a finished acesulfame potassium composition, the process comprising the steps of:

(a) providing a cyclizing agent composition comprising a cyclizing agent and a solvent and having an initial temperature;

(b) cooling the cyclizing agent composition to form a cooled cyclizing agent composition having a cooled temperature less than 35° C.;

(c) reacting an acetoacetamide salt with the cyclizing agent in the cooled cyclizing agent composition to form a cyclic sulfur trioxide adduct composition comprising cyclic sulfur trioxide adduct; and (d) forming the finished acesulfame potassium composition from the cyclic sulfur trioxide adduct in the cyclic sulfur trioxide adduct composition, wherein the finished acesulfame potassium composition comprises non-chlorinated acesulfame potassium and less than 39 wppm 5-chloro-acesulfame potassium;

wherein the cooled temperature is at least 2° C. less than the initial temperature.

Aspect 2: The process of aspect 1, wherein the forming comprises:

hydrolyzing the cyclic sulfur trioxide adduct in the cyclic sulfur trioxide adduct composition to form an acesulfame-H composition; and neutralizing the acesulfame-H in the acesulfame H composition to form a crude acesulfame potassium composition comprising non-chlorinated acesulfame potassium and less than 39 wppm 5-chloro-acesulfame potassium; and forming the finished acesulfame potassium composition from the crude acesulfame potassium composition.

Aspect 3: The process of any one of the preceding aspects, wherein the providing step (a) comprises the step of contacting the solvent and the cyclizing agent to form the cyclizing agent composition; and wherein a contact time from the beginning of the contacting step to the beginning of reacting step (c) is less than 60 minutes.

Aspect 4: The process of any one of the preceding aspects, wherein the finished acesulfame potassium composition comprises from 1 wppb to 5 wppm 5-chloro-acesulfame potassium.

Aspect 5: The process of any one of the preceding aspects, wherein the cooled cyclizing agent composition has a cooled temperature less than 25° C. and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 6: The process of any one of the preceding aspects, wherein the cooled cyclizing agent composition has a cooled temperature ranging from −35° C. to 15° C. and the crude acesulfame potassium composition comprises from 1 wppb to 5 wppm 5-chloro-acesulfame potassium and the finished acesulfame potassium composition comprises from 1 wppb to 2.7 wppm 5-chloro-acesulfame potassium.

Aspect 7: The process of any one of the preceding aspects, wherein the cooled cyclizing agent composition has a cooled temperature less than 25° C. and the contact time is less than 15 minutes and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 8: The process of any one of the preceding aspects, wherein the cooled cyclizing agent composition has a cooled temperature ranging from −35° C. to 15° C. and the contact time is less than 5 minutes and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 9: The process of any one of the preceding aspects, wherein the finished acesulfame potassium composition comprises at least 90% by weight of the 5-chloro-acesulfame potassium present in the crude acesulfame potassium composition.

Aspect 10: The process of any one of the preceding aspects, wherein the finished acesulfame potassium composition comprises at least 90% by weight of the 5-chloro-acesulfame potassium present in the crude acesulfame potassium composition.

Aspect 11: The process of any one of the preceding aspects, wherein the forming of the finished acesulfame potassium composition from the crude acesulfame potassium composition comprises the steps of: concentrating the crude acesulfame composition to form an intermediate acesulfame potassium composition comprising at least 10 wt % acesulfame potassium; and separating the intermediate acesulfame potassium composition to form the finished acesulfame potassium composition comprising at least 15 wt % acesulfame potassium.

Aspect 12: The process of any one of the preceding aspects, wherein the cooled cyclizing agent composition comprises less than 1 wt % cyclizing agent/solvent reaction product selected from the group consisting of chloromethyl chlorosulfate and methyl-bis-chlorosulfate.

Aspect 13: The process of any one of the preceding aspects, wherein the weight ratio of solvent to cyclizing agent in the cyclizing agent composition is at least 1:1.

Aspect 14: A process for producing a finished acesulfame potassium composition, the process comprising the steps of:

(a) cooling a solvent;
(b) combining the cooled solvent with a cyclizing agent to form a cooled cyclizing agent composition having a cooled temperature less than 35° C.;
(c) reacting an acetoacetamide salt with the cyclizing agent in the cyclizing agent composition to form a cyclic sulfur trioxide adduct composition comprising a sulfur trioxide adduct; and
(d) forming the finished acesulfame potassium composition from the cyclic sulfur trioxide adduct composition, wherein the finished acesulfame potassium composition comprises non-chlorinated acesulfame potassium and less than 39 wppm 5-chloro acesulfame potassium.

Aspect 15: The process of aspect 14, wherein the finished acesulfame potassium composition comprises from 1 wppb to 5 wppm chloro-acesulfame potassium.

Aspect 16: A process for producing a finished acesulfame potassium composition, the process comprising the steps of:

(a) providing a cyclic sulfur trioxide adduct composition comprising one or more of chloromethyl chlorosulfate and methyl-bis-chlorosulfate present in a collective amount less than 1 wt %; and
(b) forming the finished acesulfame potassium composition from the cyclic sulfur trioxide adduct composition, wherein the finished acesulfame potassium composition comprises non-chlorinated acesulfame potassium and less than 39 wppm 5-chloro-acesulfame potassium.

Aspect 17: The process of aspect 16, wherein the acesulfame potassium composition comprises from 1 wppb to 5 wppm 5-chloro-acesulfame potassium.

Aspect 18: The process of aspect 16 or 17, wherein the providing step (a) comprises reacting sulfamic acid and triethylamine to form an amidosulfamic acid salt;

reacting the amidosulfamic acid salt and diketene to form acetoacetamide salt;

providing a cyclizing agent composition comprising a sulfur trioxide and dichloromethane and having an initial temperature;

cooling the cyclizing agent composition to form a cooled cyclizing agent composition having a cooled temperature below 35° C.;

reacting the acetoacetamide salt with sulfur trioxide in the cooled cyclizing agent composition to form the cyclic sulfur trioxide adduct composition;

wherein the cooled temperature is at least 2° C. less than the initial temperature.

Aspect 19: The process of aspect 16-18, wherein the providing step comprises the step of contacting the solvent and the cyclizing agent to form the cyclizing agent composition and a contact time from the beginning of the contacting step to the beginning of the reacting step is less than 15 minutes, and wherein the cooled cyclizing agent composition has a cooled temperature less than 25° C. and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 20: The process of aspect 16-19, wherein the providing step comprises the step of contacting the solvent and the cyclizing agent to form the cyclizing agent composition and a contact time from the beginning of the contacting step to the beginning of the reacting step is less than 5 minutes, and wherein the cooled cyclizing agent composition has a cooled temperature ranging from −35° C. to 15° C. and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 21: A process for producing a finished acesulfame potassium composition, the process comprising the steps of:
(a) reacting sulfamic acid and triethylamine to form an amidosulfamic acid salt;
(b) reacting the amidosulfamic acid salt and diketene to form acetoacetamide salt;
(c) providing a cyclizing agent composition comprising a sulfur trioxide and dichloromethane and having an initial temperature;
(d) cooling the cyclizing agent composition to form a cooled cyclizing agent composition having a cooled temperature less than 35° C.;
(e) reacting the acetoacetamide salt with sulfur trioxide in the cooled cyclizing agent composition to form a cyclic sulfur trioxide adduct;
(f) hydrolyzing the cyclic sulfur trioxide adduct to form an acesulfame-H composition comprising acesulfame-H;
(g) neutralizing the acesulfame-H in the acesulfame-H to form a crude acesulfame potassium composition comprising non-chlorinated acesulfame potassium and from 1 wppb to 39 wppm 5-chloro-acesulfame potassium acid,
(h) treating the crude acesulfame potassium composition to form the finished acesulfame potassium composition comprising acesulfame potassium and less than 37 wppm acetoacetamide-N-sulfonic acid,
wherein steps (a), (b), (c), and (d) can be performed in any order before the performance of step (e) and wherein the cooled temperature is at least 2° C. less than the initial temperature, and wherein the providing step (c) comprises the step of contacting the solvent and the cyclizing agent to form the cyclizing agent composition; and wherein a contact time from the beginning of the contacting step to the beginning of reacting step (e) is less than 60 minutes.

Aspect 22: The process of aspect 21, wherein contact time from the beginning of the contacting step to the beginning of the reacting step (e) is less than 15 minutes, and wherein the cooled cyclizing agent composition has a cooled temperature less than 25° C. and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 23: The process of aspect 21 or 22, wherein contact time from the beginning of the contacting step to the beginning of the reacting step (e) is less than 5 minutes, and wherein the cooled cyclizing agent composition has a cooled temperature ranging from −35° C. to 15° C. and the crude acesulfame potassium composition comprises from 1 wppb to 39 wppm 5-chloro-acesulfame potassium and the finished acesulfame potassium composition comprises from 1 wppb to 5 wppm 5-chloro-acesulfame potassium.

Aspect 24: A finished acesulfame potassium composition produced or producible by, or obtainable or obtained from the process of any one of aspects 1 to 23.

EXAMPLES

Examples 1-3 and Comparative Example A 100 mmol of 99.5% pure sulfamic acid was suspended in 50 mL dichloromethane in a flask with reflux. Under continuous agitation, 105 mmol of trimethylamine was added within approximately 3 minutes. During this time, temperature increased due to acid/base exothermal reaction up to about 42° C. (the boiling point of dichloromethane). This first reaction mixture was stirred for approximately 15 additional minutes, until no solid sedimentation was seen in the flask. Then, 10 mmol of acetic acid was added to the first reaction mixture and was stirred for approximately 15 additional minutes. At this point, within 7 minutes of the addition of the acetic acid, 110 mmol of diketene was added dropwise to form a second reaction mixture. After the addition of all of the diketene was added to the second reaction mixture and approximately 15 minutes of reaction time, this second reaction mixture was cooled. The resultant cooled second reaction mixture contained approximately 30% acetoacetamide N-sulfonate triethylammonium salt. Additional batches of cooled second reaction mixture were prepared as necessary. The acetoacetamide N-sulfonate triethylammonium salt was used as discussed below.

Sulfur trioxide/dichloromethane compositions (cyclizing agent compositions) were prepared by contacting approximately 15 wt % sulfur trioxide and approximately 85 wt % dichloromethane with one another in a flask.

For Examples 1-3, the initial sulfur trioxide/dichloromethane compositions were cooled from approximately 25° C. to lower temperatures by placing the respective flask in a cooling bath containing a mixture of isopropanol and dry ice before the cyclization reaction. For the Comparative Example, the sulfur trioxide/dichloromethane composition was warmed from approximately 25° C. to higher temperature by placing the respective flask in a warm water bath before the cyclization reaction. The cooled temperatures of the sulfur trioxide/dichloromethane compositions for Examples 1-3 and the (warmed) temperature of the sulfur trioxide/dichloromethane composition of Comparative Example A are shown in Table 1.

For Examples 1-3 and Comparative Example A, a reaction flask (a 4 necked round bottom flask equipped with mechanical stirrer, thermometer, and feed vessels) was placed into a cooling bath containing a mixture of isopropanol and dry ice. Approximately 200 g of the acetoacetamide-N-sulfonate triethylammonium salt solution and approximately 577 g of the sulfur trioxide/dichloromethane compositions were measured.

The sulfur trioxide/dichloromethane compositions were held for various time periods before the start of the cyclization reaction. Approximately 15 wt % of the total sulfur trioxide/dichloromethane composition (approximately 87 g) was initially fed to the reaction flask under continuous agitation by mechanical stirrer. When the temperature of the reaction flask contents reached −35° C. (due to the cooling batch), the remainder of the sulfur trioxide/dichloromethane composition and all of the acetoacetamide-N-sulfonate triethylammonium salt solution were fed into the reaction flask. Contact times (the time periods that the solvent contacted the cyclizing agent before formation of the cyclic sulfur trioxide adduct, e.g., before the acetoacetamide-N-sulfonate triethylammonium salt solution was fed to the reaction flask) for the respective Examples 1-3 and Comparative Example A are shown in Table 1. The feed rate was controlled in such a way that the temperature of the reaction flask contents remained between −25° and −35° C. during the feeding/cyclization reaction. After the reactants were fed, the reaction was allowed to proceed for approximately one additional minute. The cooling bath was then removed.

After approximately one minute, the temperature of the reaction flask contents reached approximately −22° C. At this time, hydrolysis was initiated by feeding deionized water to the reaction flask. Water was fed over 10 minutes.

The hydrolysis reaction was exothermic. Water was added slowly so as to maintain temperature between −20° C. and −5° C. After addition of water, reaction mixture was allowed to reach room temperature.

The hydrolyzed product was phase separated via a separating funnel. A heavier organic sweetener acid-dichloromethane phase (acesulfame-H composition) was separated out, and the remaining aqueous phase was discarded.

The acesulfame-H in the acesulfame-H composition was neutralized with a 10% potassium hydroxide solution. Neutralization was carried out at 25° C.±1° C. Potassium hydroxide addition was completed within 20 minutes.

After completion of the neutralization step, an additional phase separation was performed using a separating funnel to yield an aqueous phase containing acesulfame potassium (and some impurities) and an organic phase. The aqueous phase is considered a crude acesulfame potassium composition. The aqueous phase analyzed for impurities, e.g., 5-chloro acesulfame potassium. Testing for 5-chloro-acesulfame potassium was performed using the HPLC equipment and techniques discussed herein. In particular, the HPLC analysis was performed using an LC Systems HPLC unit from Shimadzu having a CBM-20 Shimadzu controller and being equipped with a CC 250/4.6 Nucleodur 100-3 C18 ec (250×4.6 mm) MACHEREY NAGEL column. A Shimadzu SPD-M20A photodiode array detector was used for detection (at 234 nm wavelength). Analysis was performed at 23° C. column temperature. As an eluent solution, an aqueous solution of tetra butyl ammonium hydrogen sulfate (3.4 g/L and 60% of the total solution) and acetonitrile (HPLC grade) (300 mL/L and 40% of the total solution) was employed. Elution was isocratic. The overall flow rate of total eluent was approximately 1 mL/min. The data collection and calculations were performed using Lab Solution software from Shimadzu. The remaining dichloromethane phase was discarded. The results of the impurity analysis for Examples 1-3 and Comparative Example A are shown in Table 1.

Example 4

Liquid sulfur trioxide and dichloromethane were continuously fed, contacted to form a cyclizing agent composition, and cooled into a static mixer at 1220 kg/h and 8000 kg/h, respectively. The temperature of the cooled cyclizing agent composition was 11° C. The mixture was held in the static mixture for less than 5 minutes and then fed into a cyclization reactor, thus contact time was less than 5 minutes. In the cyclization reactor the cooled sulfur trioxide/diclhloromethane composition was reacted with a solution of acetoacetamide-N-sulfonate triethylammonium salt (acetoacetamide salt) in dichloromethane. The resultant cyclized product was hydrolyzed and worked up to yield a crude acesulfame potassium composition comprising (non-chlorinated) acesulfame potassium. The crude acesulfame potassium was analyzed using the HPLC equipment and techniques discussed above. With a detection limit of 1 wppm, no 5-chloro-acesulfame potassium was detected. The results of the impurity analysis of Example 4 is also shown in Table 2.

TABLE 1

5-chloro Acesulfame Potassium Content
in Crude Acesulfame Potassium Compositions

| Ex./Comp. Ex. | Contact Time, min. | Cooled Temperature, ° C. | Temperature Change, ° C. | 5-chloro Ace-K, wppm |
|---|---|---|---|---|
| Ex. 1 | 60 | 5° C. | −20° C. | 32 |
| Ex. 2 | 30 | 5° C. | −20° C. | 23 |
| Ex. 3 | 30 | 22° C. | −3° C. | 33 |
| Ex. 4 | <5 | 11° C. | — | Not detectable |
| Comp. Ex. A | 60 | 35° C. | +10° C. | 39 |

As shown in the Examples, 5-chloro-acesulfame potassium content was affected by the cooling of the sulfur trioxide/dichloromethane compositions prior to reaction to form the cyclic sulfur trioxide adduct. When the initial temperature of the sulfur trioxide/dichloromethane compositions was cooled to a cooler temperature by 2° C. or more, 5-chloro-acesulfame potassium content in the crude acesulfame potassium composition was reduced. In contrast, when a cooling step was not utilized (or when the sulfur trioxide/dichloromethane composition was actually warmed), 5-chloro-acesulfame potassium content in the crude acesulfame potassium was significantly greater (see Comparative Example A).

In addition, 5-chloro-acesulfame potassium content was affected by contact time. In particular, when short contact times and larger cooling differentials were utilized, 5-chloro-acesulfame potassium content was significantly reduced (see Exs. 2 and 4).

Only minor and simple additional purifications of the crude acesulfame composition were necessary to form the finished acesulfame potassium compositions. Approximately 50% of water was evaporated out of the crude acesulfame potassium compositions in roti vapor at reduced pressure. The resultant concentrated acesulfame potassium composition was then cooled in a refrigerator at +5° C., which led to precipitation of "crude crystals" containing mostly acesulfame potassium. The crude crystals were then dissolved in enough water and this resultant solution was heated to 70° C. Activated carbon powder was then added to the solution. The solution (with the added activated carbon) was then filtered.

The filtrate that was yielded from the filtration was cooled to room temperature, which led to the formation of "intermediate crystals" containing mostly acesulfame potassium. The intermediate crystals were dissolved in sufficient water and heated to 70° C. in a water bath.

Activated carbon was added to this solution (of intermediate crystals and activated carbon). This solution was then filtered. When filtrate was cooled down to room temperature, white-colored "pure crystals" of acesulfame potassium were formed.

These pure crystals are considered the finished acesulfame potassium composition. Testing for 5-chloro-acesulfame potassium was performed using the HPLC equipment and techniques discussed above. The crystals of the finished acesulfame potassium composition contained the same amount (or slightly lower amounts) of 5-chloro-acesulfame potassium.

The purification steps did not show a marked reduction in 5-chloro-acesulfame potassium content. It is believed that because the chemical structure of chloro-acesulfame potassium is similar to that of acesulfame potassium, separation of chloro-acesulfame potassium using standard purification procedures such as crystallization is ineffective. This analysis demonstrates the importance of reducing/eliminating the production of 5-chloro-acesulfame potassium during the steps leading to the formation of the crude acesulfame composition as described herein.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing a finished acesulfame potassium composition, the process comprising:
   reacting an acetoacetamide salt with a cyclizing agent composition having a temperature of from −15° C. to 25° C., wherein the cyclizing agent composition comprises a sulfur trioxide and a solvent, and wherein the reacting of the acetoacetamide salt with the cyclizing composition forms a cyclic sulfur trioxide adduct composition comprising cyclic sulfur trioxide adduct, wherein the cyclization reaction time less than 35 minutes; and
   forming a finished acesulfame potassium composition from the cyclic sulfur trioxide adduct, wherein the finished acesulfame composition comprises non-chlorinated acesulfame potassium and less than 39 wppm 5-chloro-acesulfame potassium.

2. The process of claim 1, wherein the forming of the finished acesulfame potassium composition comprises:
   concentrating a crude acesulfame composition to form an intermediate acesulfame potassium composition comprising at least 10 wt % acesulfame potassium; and
   separating the intermediate acesulfame potassium composition to form the finished acesulfame potassium composition comprising at least 15 wt % acesulfame potassium.

3. The process of claim 1, wherein the weight ratio of solvent to cyclizing agent in the cyclizing agent composition is at least 1:1.

4. A finished acesulfame potassium composition produced by the process claim 1.

5. The process of claim 1, wherein the finished acesulfame potassium composition comprises from 1 wppb to 5 wppm 5-chloro-acesulfame potassium.

6. The process of claim 1, wherein the finished acesulfame potassium composition comprises from 1 wppb to 2.7 wppm 5-chloro-acesulfame potassium.

7. The process of claim 1, further comprising:
   hydrolyzing the cyclic sulfur trioxide adduct in the cyclic sulfur trioxide adduct composition to form an acesulfame-H composition;
   neutralizing the acesulfame-H in the acesulfame-H composition to form a crude acesulfame potassium composition comprising non-chlorinated acesulfame potassium; and
   forming the finished acesulfame potassium composition from the crude acesulfame potassium composition.

8. The process of claim 7, wherein the crude acesulfame potassium composition comprises from 1 wppb to 39 wppm 5-chloro-acesulfame potassium.

9. The process of claim 7, wherein the crude acesulfame potassium composition comprises from 1 wppb to 5 wppm 5-chloro-acesulfame potassium.

10. The process of claim 1, wherein the solvent includes dichloromethane.

11. The process of claim 1, wherein the cyclizing agent composition comprises less than 1 wt % of a cyclizing agent/solvent reaction product that includes chloromethyl chlorosulfate, methyl-bis-chlorosulfate, or a combination thereof.

12. The process of claim 1, wherein the cyclizing agent and the solvent are contacted to form the cyclizing agent composition.

13. The process of claim 12, wherein the cyclizing agent and the solvent are contacted for less than 15 minutes prior to reacting the acetoacetamide salt with the cyclizing agent composition.

14. The process of claim 1, further comprising forming the cyclizing agent composition by a process that includes cooling the solvent and thereafter contacting the cooled solvent with the cyclizing agent.

15. The process of claim 1, further comprising forming the cyclizing agent composition by a process that includes contacting the solvent with the cyclizing agent to form an initial cyclizing agent composition, and thereafter cooling the cyclizing agent composition to a temperature of from −15° C. to 25° C.

16. The process of claim 15, wherein the cooled cyclizing agent composition has a temperature of at least 2° C. less than the temperature of the initial cyclizing agent composition.

17. The process of claim 1, further comprising forming the acetoacetamide salt by a process that comprises reacting sulfamic acid and triethylamine to form an amidosulfamic acid salt, and reacting the amidosulfamic acid salt and a diketene to the form acetoacetamide salt.

* * * * *